US012788487B2

(12) United States Patent
Melsky et al.

(10) Patent No.: US 12,788,487 B2
(45) Date of Patent: Nov. 10, 2026

(54) ABLATION CATHETERS WITH MULTIPLE ENDOSCOPES AND IMAGING CHIP ENDOSCOPES AND SYSTEM FOR ALTERING AN ORIENTATION OF AN ENDOSCOPIC IMAGE

(71) Applicant: CARDIOFOCUS, INC., Marlborough, MA (US)

(72) Inventors: Gerald Melsky, Lexington, MA (US); Lincoln Baxter, Centerville, MA (US); Brian Estabrook, Foxboro, MA (US); Susan Ostrowski, Burlington, MA (US)

(73) Assignee: CARDIOFOCUS, INC., Marlborough, MA (US)

(*) Notice: Subject to any disclaimer, the term of this patent is extended or adjusted under 35 U.S.C. 154(b) by 291 days.

(21) Appl. No.: 18/489,523

(22) Filed: Oct. 18, 2023

(65) Prior Publication Data

US 2024/0041525 A1 Feb. 8, 2024

Related U.S. Application Data

(62) Division of application No. 17/524,472, filed on Nov. 11, 2021, now abandoned.

(Continued)

(51) Int. Cl.
*A61B 18/24* (2006.01)
*A61B 1/00* (2006.01)

(Continued)

(52) U.S. Cl.
CPC .......... *A61B 18/24* (2013.01); *A61B 1/00183* (2013.01); *A61B 90/37* (2016.02);

(Continued)

(58) Field of Classification Search
CPC ..... A61B 18/24; A61B 1/00183; A61B 90/37; A61B 1/043; A61B 5/0084;

(Continued)

(56) References Cited

U.S. PATENT DOCUMENTS 5,054,492 A * 10/1991 Scribner ................ G10K 11/35 600/463
5,542,915 A 8/1996 Edwards (Continued)

FOREIGN PATENT DOCUMENTS

CN 107260117 A 10/2017
CN 113558753 A 10/2021

(Continued)

OTHER PUBLICATIONS

Extended European Search Report in EP Application No. 21892808.3-1122/4243671, mailed Aug. 8, 2024 (7 pages).

(Continued)

*Primary Examiner* — Anhtuan T Nguyen
*Assistant Examiner* — Shankar Raj Ghimire
(74) *Attorney, Agent, or Firm* — Leason Ellis LLP

(57) ABSTRACT

An ablation catheter for performing a treatment under direct visualization of a region to be treated includes a catheter body and an energy emitter that is movable relative to the catheter body. The ablation catheter includes first and second imaging devices for providing direct visualization of the region to be treated, with the first imaging device being fixed relative to the catheter body. The first and second imaging devices can be in the form of first and second imaging chip endoscopes.

10 Claims, 19 Drawing Sheets

Related U.S. Application Data

(60) Provisional application No. 63/112,895, filed on Nov. 12, 2020.

(51) Int. Cl.
*A61B 1/04* (2006.01)
*A61B 5/00* (2006.01)
*A61B 18/00* (2006.01)
*A61B 90/00* (2016.01)

(52) U.S. Cl.
CPC ............... *A61B 1/041* (2013.01); *A61B 1/043* (2013.01); *A61B 5/0084* (2013.01); *A61B 2018/00375* (2013.01); *A61B 2018/00577* (2013.01); *A61B 2018/00982* (2013.01); *A61B 2090/376* (2016.02)

(58) Field of Classification Search
CPC A61B 2018/00375; A61B 2018/00577; A61B 2018/00982; A61B 2090/3937; A61B 2090/3966; A61B 1/00009; A61B 1/0005; A61B 1/00082; A61B 1/00179; A61B 1/00181; A61B 2018/00202; A61B 2018/00285
See application file for complete search history.

(56) References Cited

U.S. PATENT DOCUMENTS

| | | | | |
|---|---|---|---|---|
| 5,573,531 | A | 11/1996 | Gregory | |
| 5,855,546 | A | 1/1999 | Hastings | |
| 6,024,763 | A * | 2/2000 | Lenker | A61F 2/07 606/191 |
| 6,354,737 | B1 * | 3/2002 | Hufe | H04N 23/633 378/165 |
| 6,572,612 | B2 | 6/2003 | Stewart | |
| 8,668,638 | B2 * | 3/2014 | Donhowe | A61B 1/009 600/137 |
| 9,421,066 | B2 | 8/2016 | Melsky et al. | |
| 9,782,183 | B1 * | 10/2017 | Rich | A61B 17/1725 |
| 10,646,118 | B2 | 5/2020 | Kowalewski | |
| 11,389,236 | B2 * | 7/2022 | Melsky | A61B 18/1815 |
| 11,786,106 | B2 * | 10/2023 | Masaki | A61B 34/30 600/114 |
| 2001/0011161 | A1 | 8/2001 | Edwards | |
| 2003/0014048 | A1 | 1/2003 | Swanson | |
| 2005/0096647 | A1 | 5/2005 | Steinke et al. | |
| 2005/0182392 | A1 | 8/2005 | Brucker | |
| 2006/0149129 | A1 | 7/2006 | Watts et al. | |
| 2006/0276686 | A1 | 12/2006 | Tsuji | |
| 2009/0012368 | A1 | 1/2009 | Banik | |
| 2009/0177259 | A1 * | 7/2009 | Ning | A61F 2/958 604/509 |
| 2009/0231419 | A1 | 9/2009 | Bayer | |
| 2009/0248012 | A1 | 10/2009 | Maor et al. | |
| 2009/0299354 | A1 | 12/2009 | Melsky | |
| 2009/0326320 | A1 | 12/2009 | Sinofsky | |
| 2010/0286626 | A1 | 11/2010 | Petersen | |
| 2011/0082449 | A1 * | 4/2011 | Melsky | A61B 18/24 606/14 |
| 2011/0082450 | A1 * | 4/2011 | Melsky | A61B 18/24 606/14 |
| 2011/0082451 | A1 * | 4/2011 | Melsky | A61B 18/24 606/14 |
| 2011/0082452 | A1 * | 4/2011 | Melsky | A61B 18/1492 606/15 |
| 2012/0065506 | A1 | 3/2012 | Smith | |
| 2012/0215094 | A1 | 8/2012 | Rahimian et al. | |
| 2013/0004059 | A1 * | 1/2013 | Said | G06T 7/33 382/154 |
| 2013/0172742 | A1 | 7/2013 | Rankin | |
| 2013/0197363 | A1 | 8/2013 | Rankin | |
| 2013/0215249 | A1 | 8/2013 | Papalazarou et al. | |
| 2014/0012155 | A1 | 1/2014 | Flaherty | |
| 2014/0163664 | A1 | 6/2014 | Goldsmith | |
| 2014/0180068 | A1 * | 6/2014 | Spencer | A61B 8/4263 600/431 |
| 2014/0180119 | A1 | 6/2014 | Millett | |
| 2014/0350553 | A1 | 11/2014 | Okuyama | |
| 2015/0305604 | A1 | 10/2015 | Melsky | |
| 2016/0135690 | A1 | 5/2016 | Brewster | |
| 2016/0157954 | A1 * | 6/2016 | Sagon | A61B 18/24 606/14 |
| 2017/0018910 | A1 | 1/2017 | Mittelstadt | |
| 2017/0189108 | A1 | 7/2017 | Melsky | |
| 2017/0231474 | A1 | 8/2017 | Saadat | |
| 2017/0367760 | A1 | 12/2017 | Crozier et al. | |
| 2018/0184982 | A1 | 7/2018 | Basu | |
| 2019/0125447 | A1 | 5/2019 | Ben Oren | |
| 2019/0216540 | A1 | 7/2019 | Melsky | |
| 2019/0231421 | A1 | 8/2019 | Viswanathan et al. | |
| 2020/0049971 | A1 | 2/2020 | Krivopisk et al. | |
| 2020/0078101 | A1 | 3/2020 | Hunter | |
| 2020/0129218 | A1 | 4/2020 | Sliwa et al. | |
| 2020/0163707 | A1 | 5/2020 | Sliwa et al. | |
| 2020/0297415 | A1 | 9/2020 | Marshik et al. | |
| 2021/0077187 | A1 | 3/2021 | Koblish et al. | |
| 2021/0169394 | A1 | 6/2021 | Chou et al. | |
| 2021/0169567 | A1 | 6/2021 | Govari | |
| 2021/0220623 | A1 | 7/2021 | Humbert | |
| 2021/0330379 | A1 | 10/2021 | Ghaly | |
| 2021/0393338 | A1 * | 12/2021 | Graetzel | A61B 34/37 |
| 2022/0142708 | A1 | 5/2022 | Melsky | |
| 2022/0218412 | A1 | 7/2022 | De La Rama et al. | |
| 2022/0218959 | A1 | 7/2022 | Valls et al. | |
| 2022/0257093 | A1 | 8/2022 | Tarke | |
| 2022/0296297 | A1 | 9/2022 | Melsky et al. | |
| 2022/0323143 | A1 | 10/2022 | Melsky et al. | |
| 2022/0378498 | A1 | 12/2022 | Zhang et al. | |
| 2023/0088525 | A1 | 3/2023 | Ratnakar | |
| 2023/0201533 | A1 | 6/2023 | Huffer et al. | |

FOREIGN PATENT DOCUMENTS

| | | | |
|---|---|---|---|
| JP | H02286123 | A | 11/1990 |
| JP | H07227394 | A | 8/1995 |
| JP | 2002535033 | A | 10/2002 |
| JP | 2008526360 | A | 7/2008 |
| JP | 2014-210085 | A | 11/2014 |
| JP | 2018524085 | A | 8/2018 |
| JP | 2020517355 | A | 6/2020 |
| WO | 2001087173 | A2 | 11/2001 |
| WO | 2016181318 | A1 | 11/2016 |
| WO | 2016210437 | | 12/2016 |
| WO | 2021059943 | A1 | 4/2021 |

OTHER PUBLICATIONS

Non-Final Office Action in U.S. Appl. No. 17/524,472, mailed Nov. 8, 2023 (12 pages).
Final Office Action in U.S. Appl. No. 17/524,472, mailed Jun. 5, 2024 (16 pages).
Yavin. "Pulsed Field Ablation Using a Lattice Electrode for Focal Energy Delivery" 529-538. Circulation: Arrhythmia and Electrophysiology. Web. Jun. 2020; pp. 529-538; [Retrieved on Mar. 8, 2023]. Retrieved from the Internet: <url: https://www.ahajournals.org/doi/pdf/10.1161/CIRCEP.120.008580>; pp. 530, 531, 533; Figure 2; DOI: 10.1161/CIRCEP.120.008580.
Extended European Search Report in EP Application No. 22899315.0-1113/4436507, mailed Sep. 2, 2025 (9 pages).
Japanese Office action in JP Application No. 2023-555312, mailed Jul. 2, 2025, an English translation attached hereto (14 pages).
Japanese Office action in JP Application No. 2023-560578, mailed Jul. 17, 2025, an English translation attached hereto (10 pages).
Non-Final Office Action in U.S. Appl. No. 17/711,574, mailed Jul. 16, 2025 (17 pages).
International Search Report and Written Opinion in PCT Application No. PCT/US2021/058976, mailed Mar. 16, 2022.
International Search Report and Written Opinion in PCT Application No. PCT/US2025/029349, mailed Sep. 9, 2025 (26 pages).

(56) References Cited

OTHER PUBLICATIONS

Chinese Office Acton in CN Application No. 202180087445.6, mailed Apr. 22, 2026, an English Translation attached hereto (17 pages).
JP Notice of Reasons for Rejection in JP Application No. 2023-528199, mailed Jun. 5, 2026, an English translation attached hereto (21 pages).

* cited by examiner

Superior position

Anterior position

Inferior position

Posterior position

ABLATION CATHETERS WITH MULTIPLE ENDOSCOPES AND IMAGING CHIP ENDOSCOPES AND SYSTEM FOR ALTERING AN ORIENTATION OF AN ENDOSCOPIC IMAGE

CROSS REFERENCE TO RELATED APPLICATION

The present application is a divisional of U.S. patent application Ser. No. 17/524,472, filed Nov. 11, 2021, which claims priority to and the benefit of U.S. patent application Ser. No. 63/112,895, filed Nov. 12, 2020, all of which are incorporated by reference, as if expressly set forth in their respective entireties herein.

TECHNICAL FIELD

The present disclosure is directed to catheters which are introduced into the human body for the purpose of performing a treatment under direct visualization of the region to be treated and more specifically, it relates to balloon catheters introduced into the left atrium of the heart which deliver laser energy to areas of the left atrium under direct visualization for the purpose of treating a medical condition called atrial fibrillation. Most commonly, the treatment area is the region near where the pulmonary veins join the left atrium. Such a procedure is called pulmonary vein isolation. To accomplish an effective pulmonary vein isolation, laser energy must be applied to a continuous ring of tissue around the ostium of each pulmonary vein. The goal of the laser energy application is to generate scar tissue which blocks conduction of electrical signals between the pulmonary veins and the atrial chamber. In another aspect, the present disclosure describes a system that includes a catheter with endoscopic chip camera(s), an image signal processing device, an image rotation processing device, and a display device to allow the user to manipulate on the display device the real-time video stream from the endoscopic chip camera.

BACKGROUND

Current devices available for endoscopically guided laser balloon ablation for pulmonary vein isolation consist of a multi-lumen catheter with a balloon at the distal end and a handle at the proximal end. An optical fiber in one lumen delivers laser energy through the catheter into the balloon where it is then projected radially toward the balloon's surface. In addition to the laser fiber there is a fiber optic endoscope that is inserted through a second lumen of the catheter. The endoscope allows the operator of the catheter to visualize the balloon surface and thereby aim the laser energy to those portions of the balloon surface which contact the atrial tissue it is desired to treat with the laser energy. Such a system is described in Melsky et al. (U.S. Pat. No. 9,421,066 (the '066 patent) and Melsky et al. (U.S. Pat. No. 9,033,961 (the '961 patent), each of which is incorporated by reference in its entirety.

SUMMARY

In one embodiment, an ablation catheter for performing a treatment under direct visualization of a region to be treated includes a catheter body and an energy emitter that is movable relative to the catheter body. The ablation catheter includes first and second imaging devices for providing direct visualization of the region to be treated, with the first imaging device being fixed relative to the catheter body. The first and second imaging devices can be in the form of first and second imaging chip endoscopes. In one embodiment, the first imaging device and the second imaging device are fixedly coupled to the catheter body and do not move relative thereto, with the first and second imaging devices being circumferentially offset. In another embodiment, the first imaging device is fixed relative to the catheter body and the second imaging device is not fixedly coupled to the catheter body but instead is movable relative thereto. For example, the second imaging device can move both axially and rotationally relative to the catheter body. In one embodiment, the second imaging device is fixedly coupled to the energy emitter and is located distal thereto such that the second imaging device moves axially and rotationally in unison with the energy emitter.

A system and method for altering orientation of an endoscopic image. An image of a catheter configured with a first marker is captured and provided during a surgical procedure. A second marker that corresponds to the first marker is rotatable via a graphical user interface (GUI) control. In response to a selection in the GUI, the second marker orientation is altered to match the catheter orientation. A first shape representing an obstructed portion of the endoscopic image, is provided in a respective orientation, and a rotatable second shape is provided in an orientation that is different than the first shape. In response to a selection received in the GUI, the orientation of the second shape is altered to match the orientation of the first shape. Thereafter, the orientation of the endoscopic image provided on a display device is altered as a function of the altered orientation of the second shape.

BRIEF DESCRIPTION OF THE DRAWING FIGURES

For the purpose of illustrating the invention, there are depicted in drawings certain embodiments of the invention. However, the invention is not limited to the precise arrangements and instrumentalities of the embodiments depicted in the drawings.

Figure 4A:
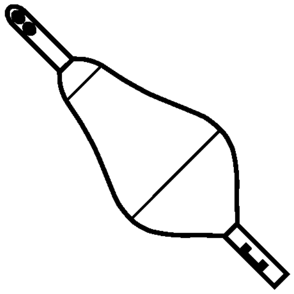
Figure 4B:
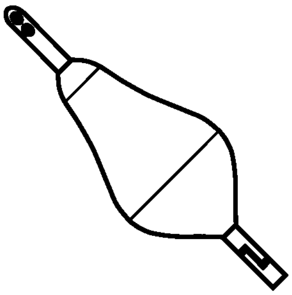
Figure 4C:
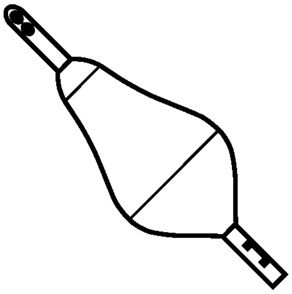
Figure 4D:
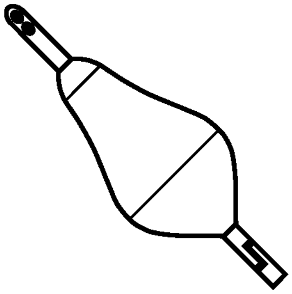
Figure 5A:
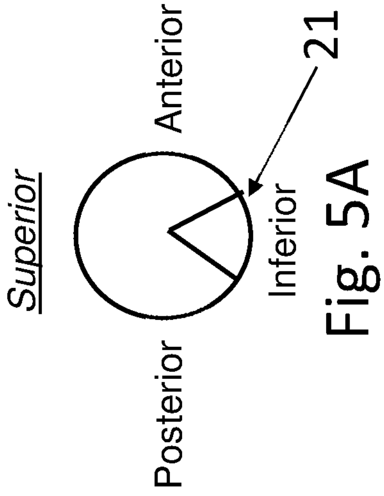
Figure 5B:
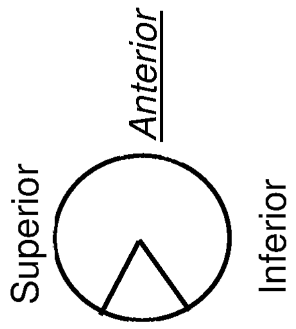
Figure 5C:
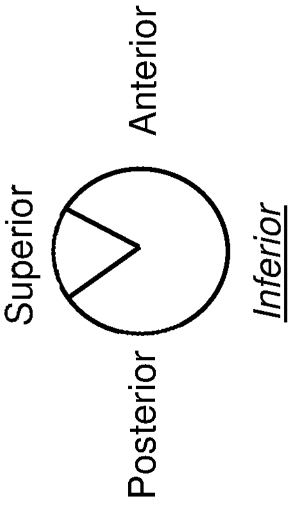
Figure 5D:
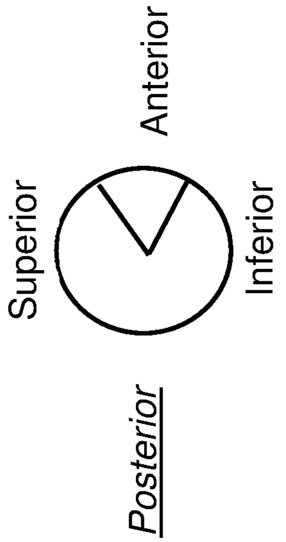
Figure 6:
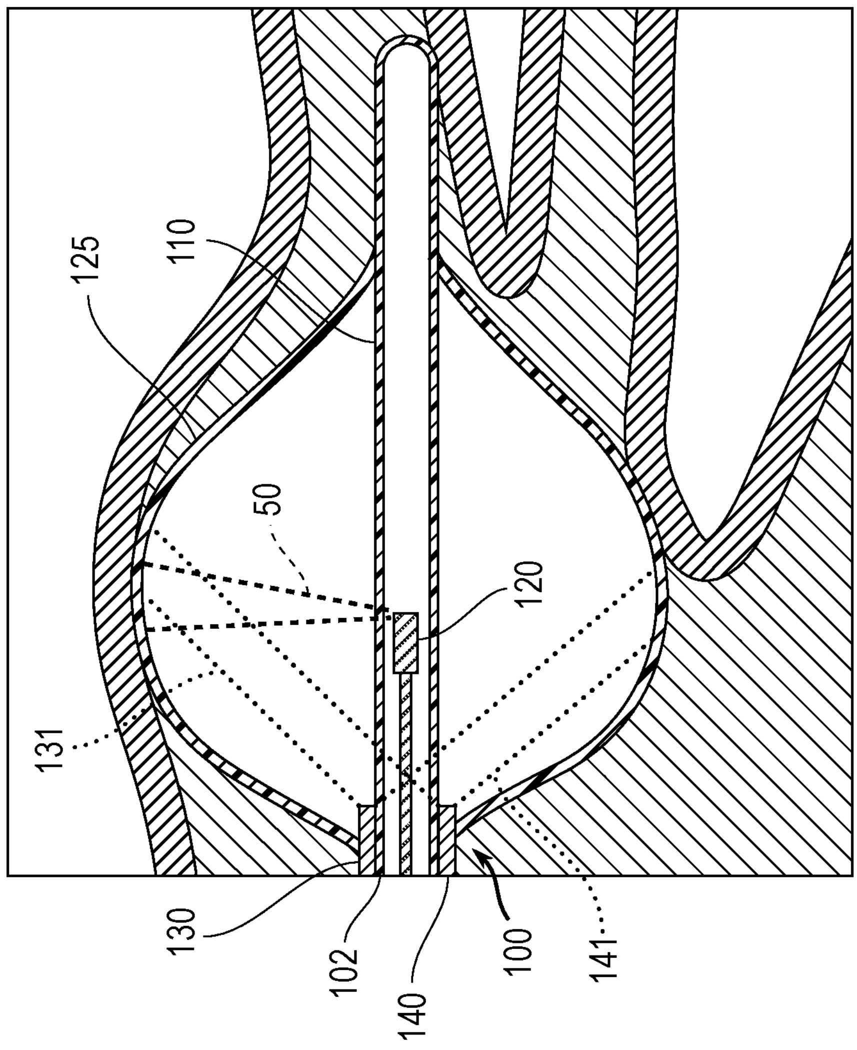
Figure 7A:
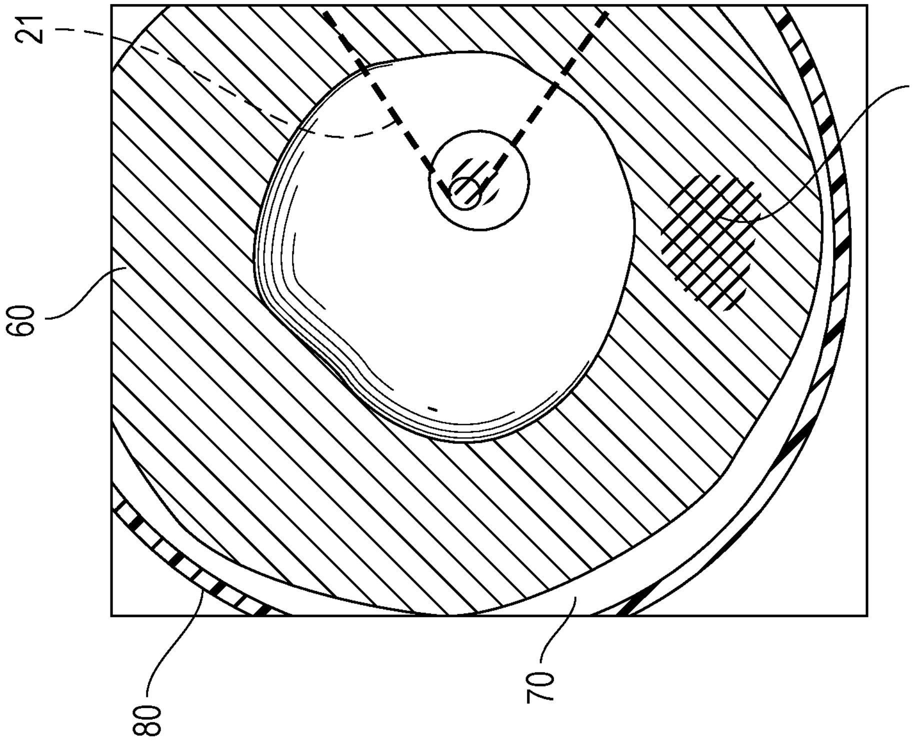
Figure 7B:
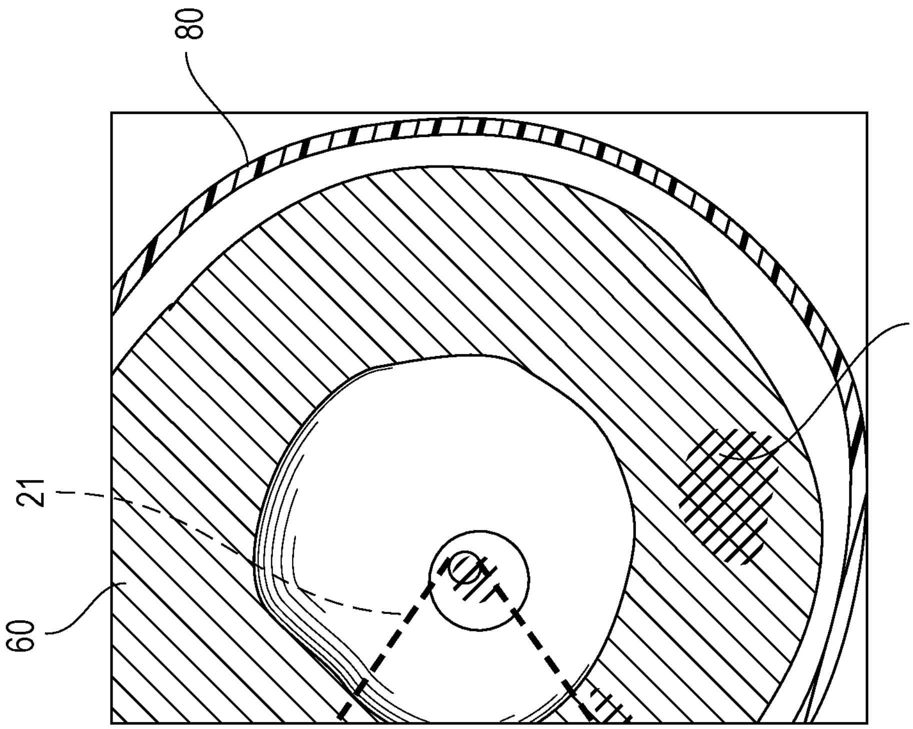
Figure 8B:
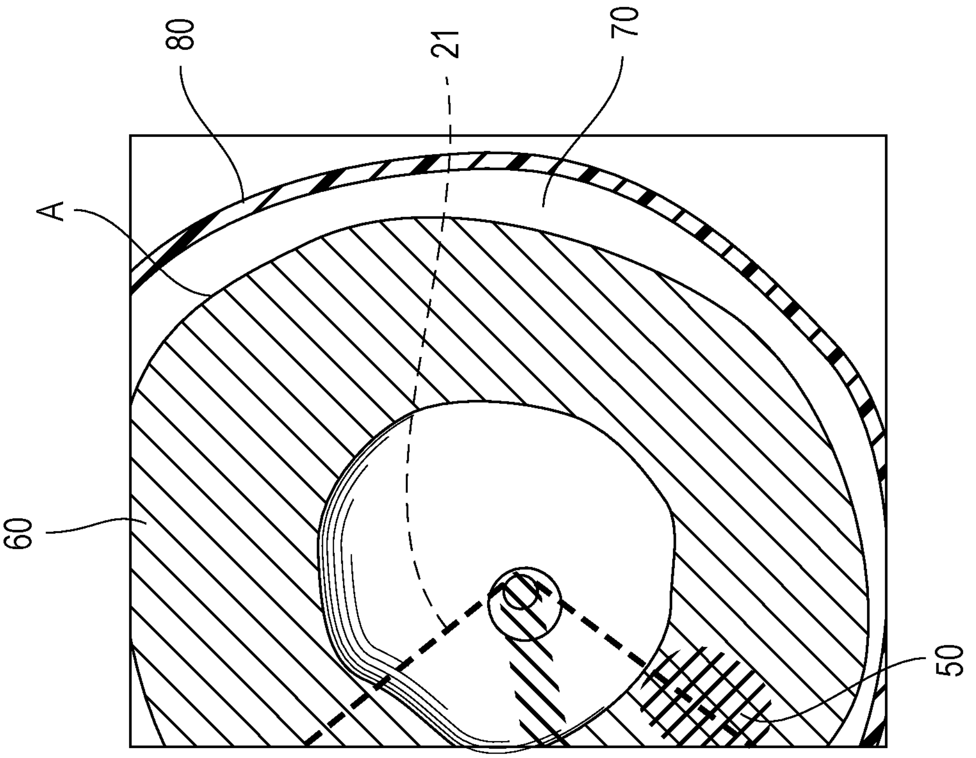
Figure 8A:
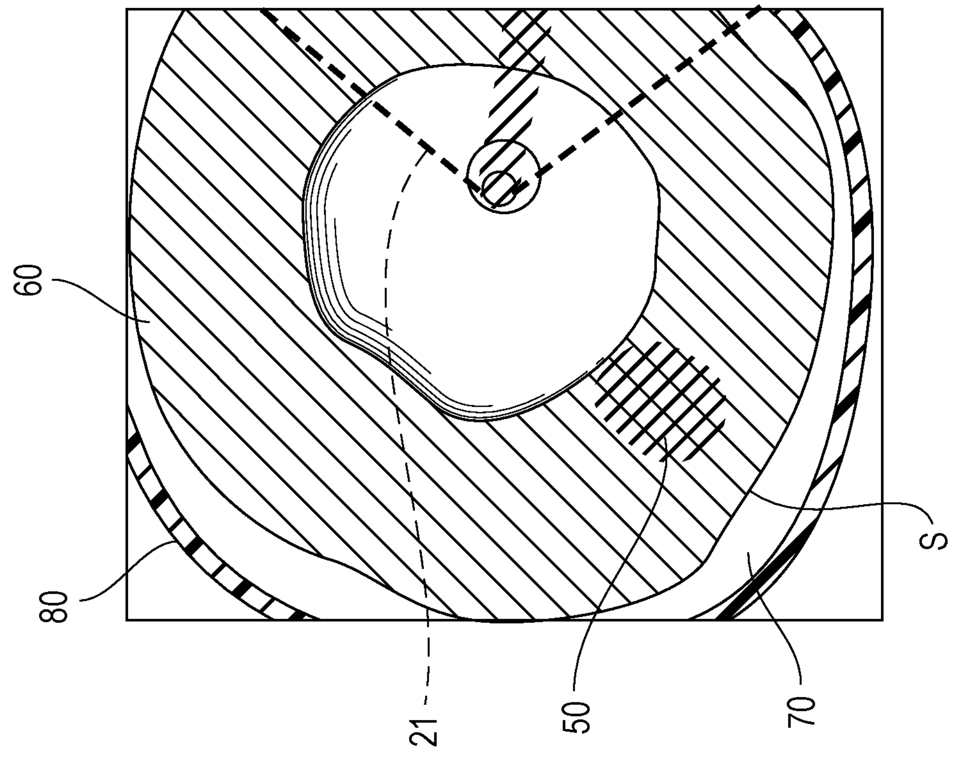
Figure 9B:
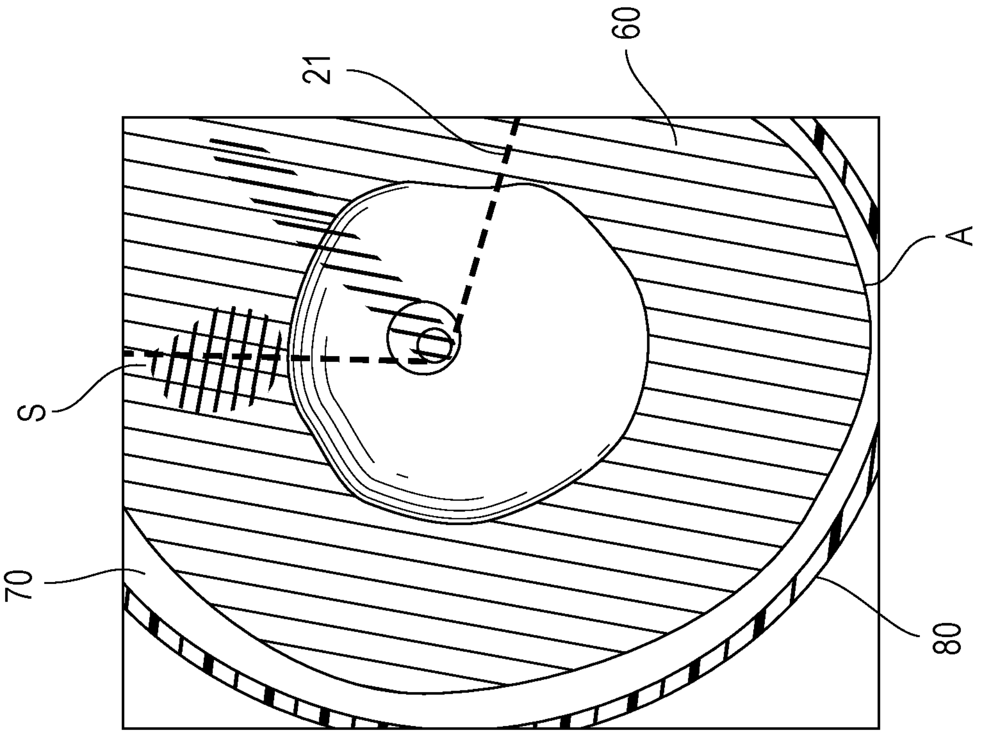
Figure 9A:
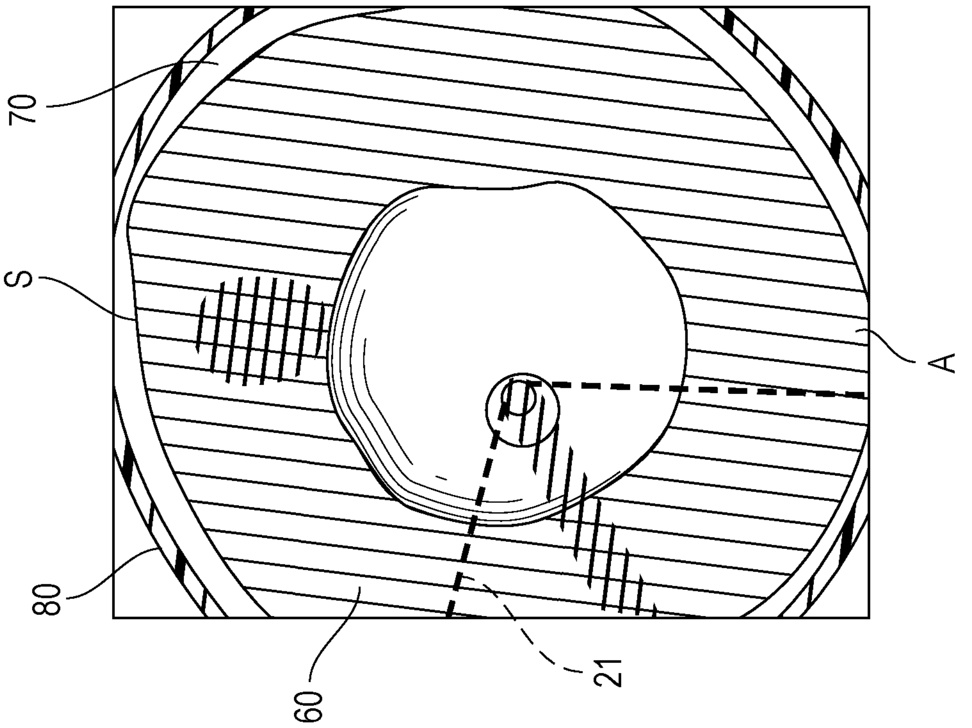
Figures 9C, 9D:
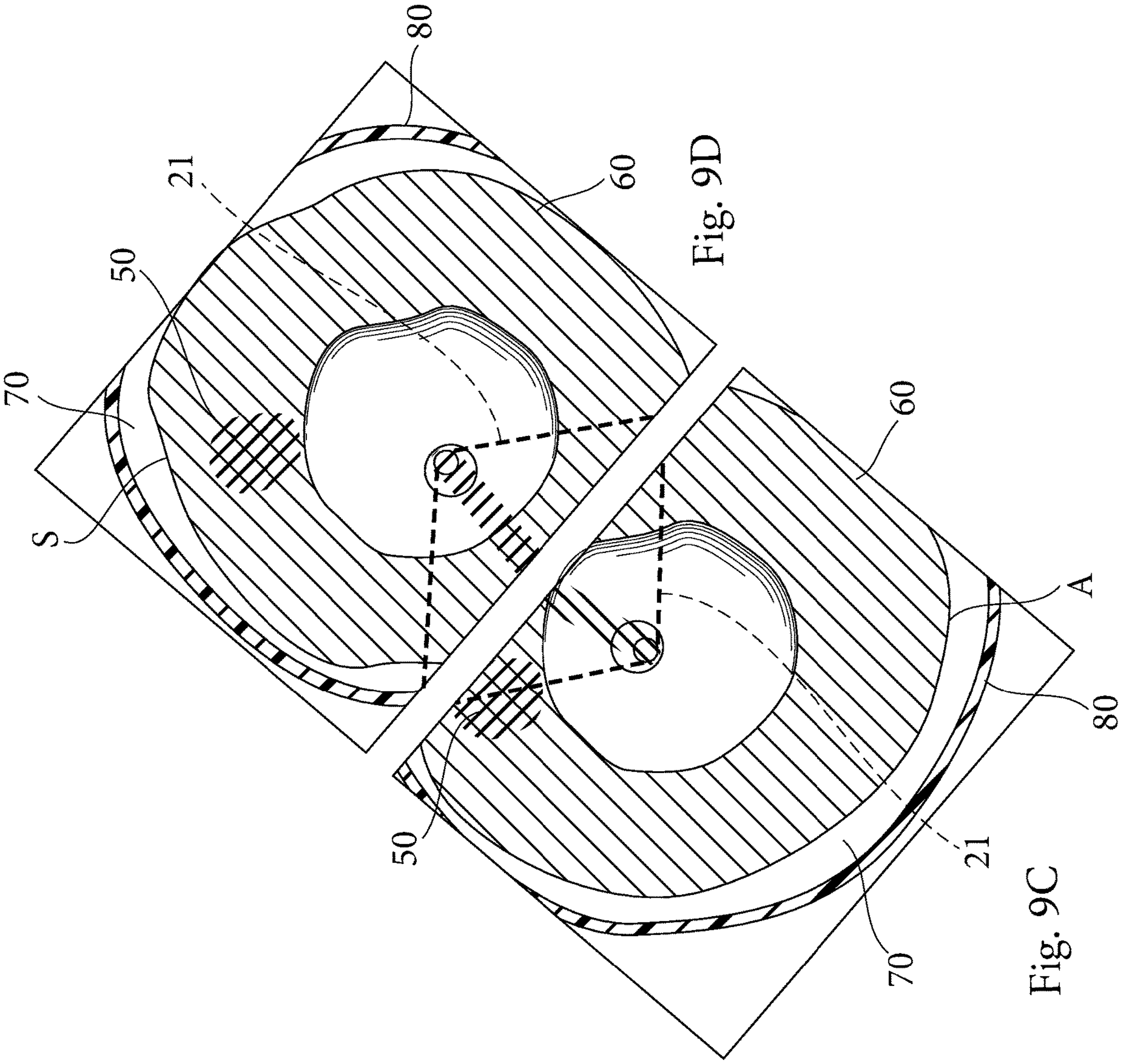
Figure 10:
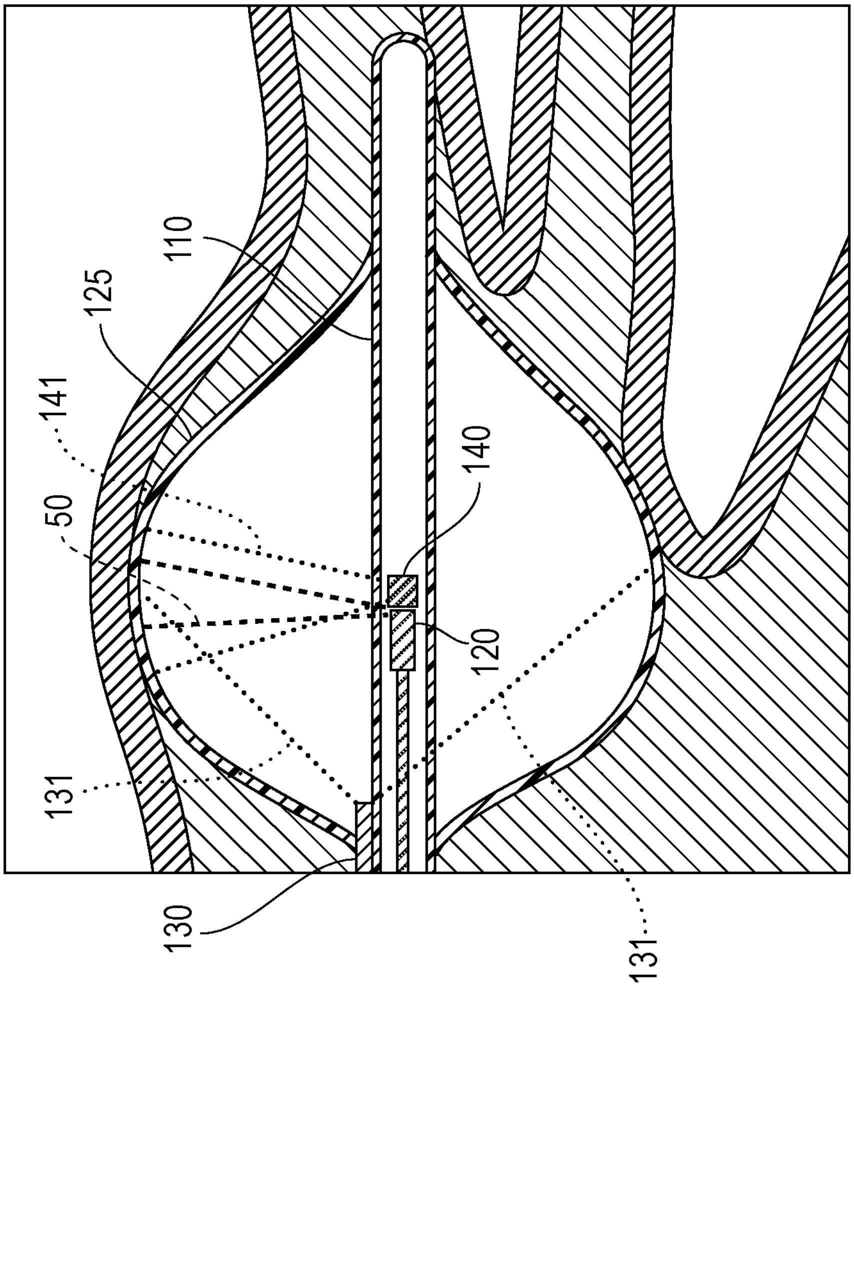
Figure 11A:
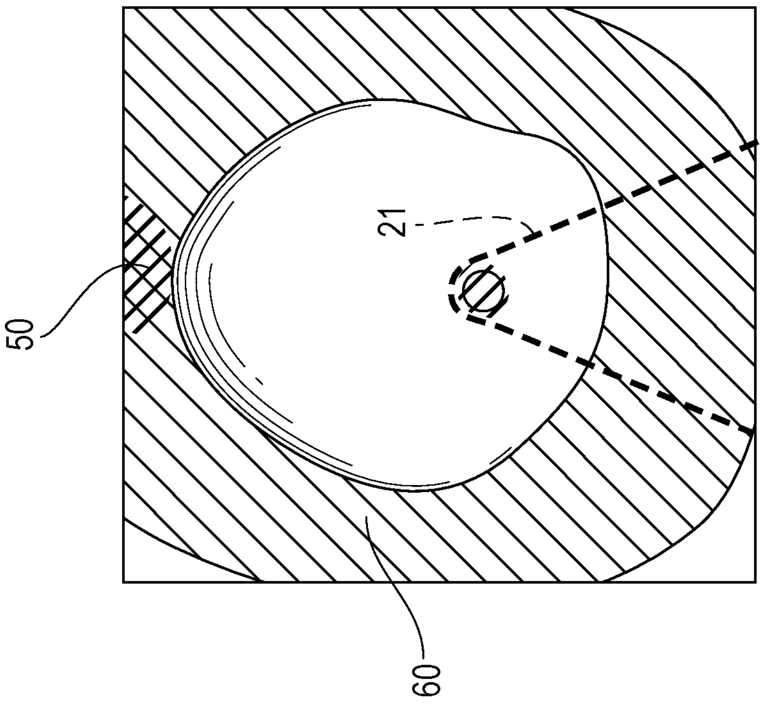
Figure 11B:
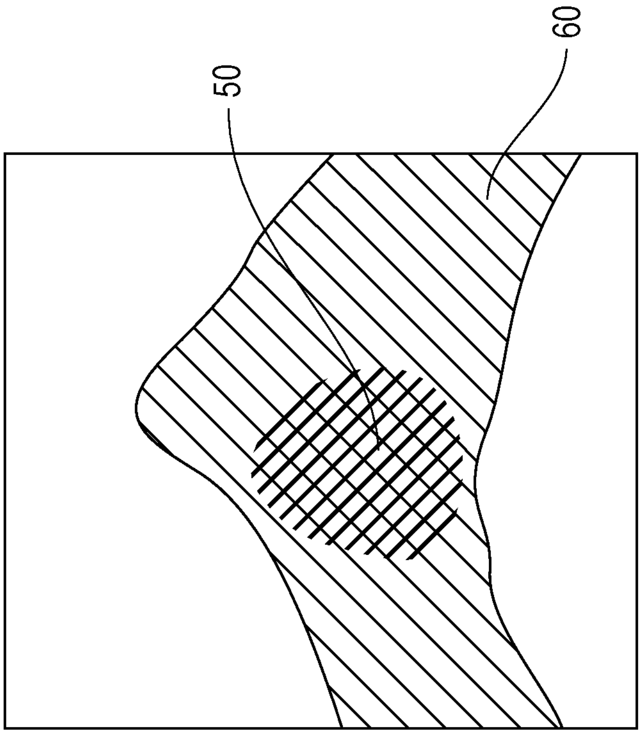
Figure 12:
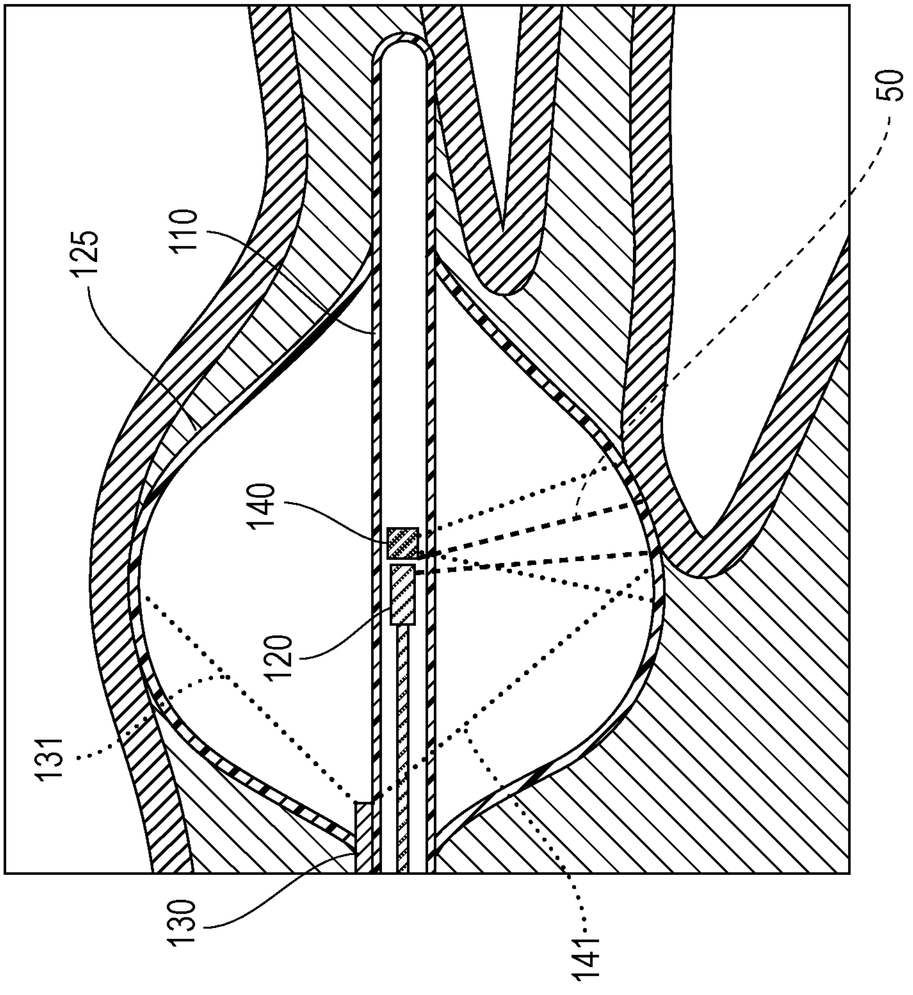
Figure 13A:
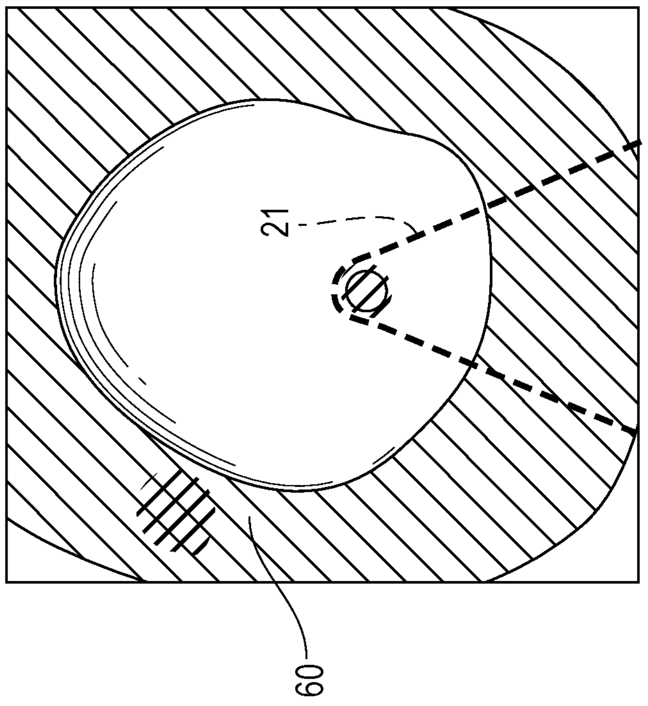
Figure 13B:
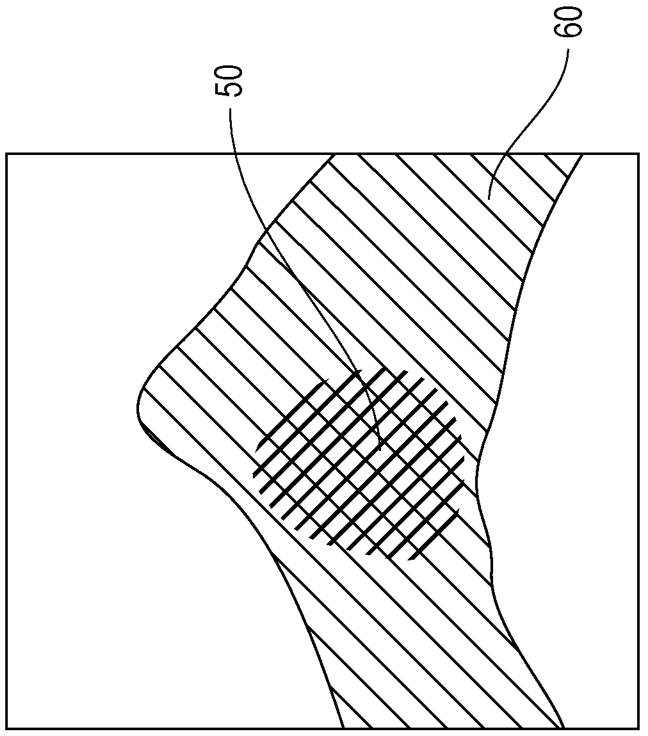
Figure 14:
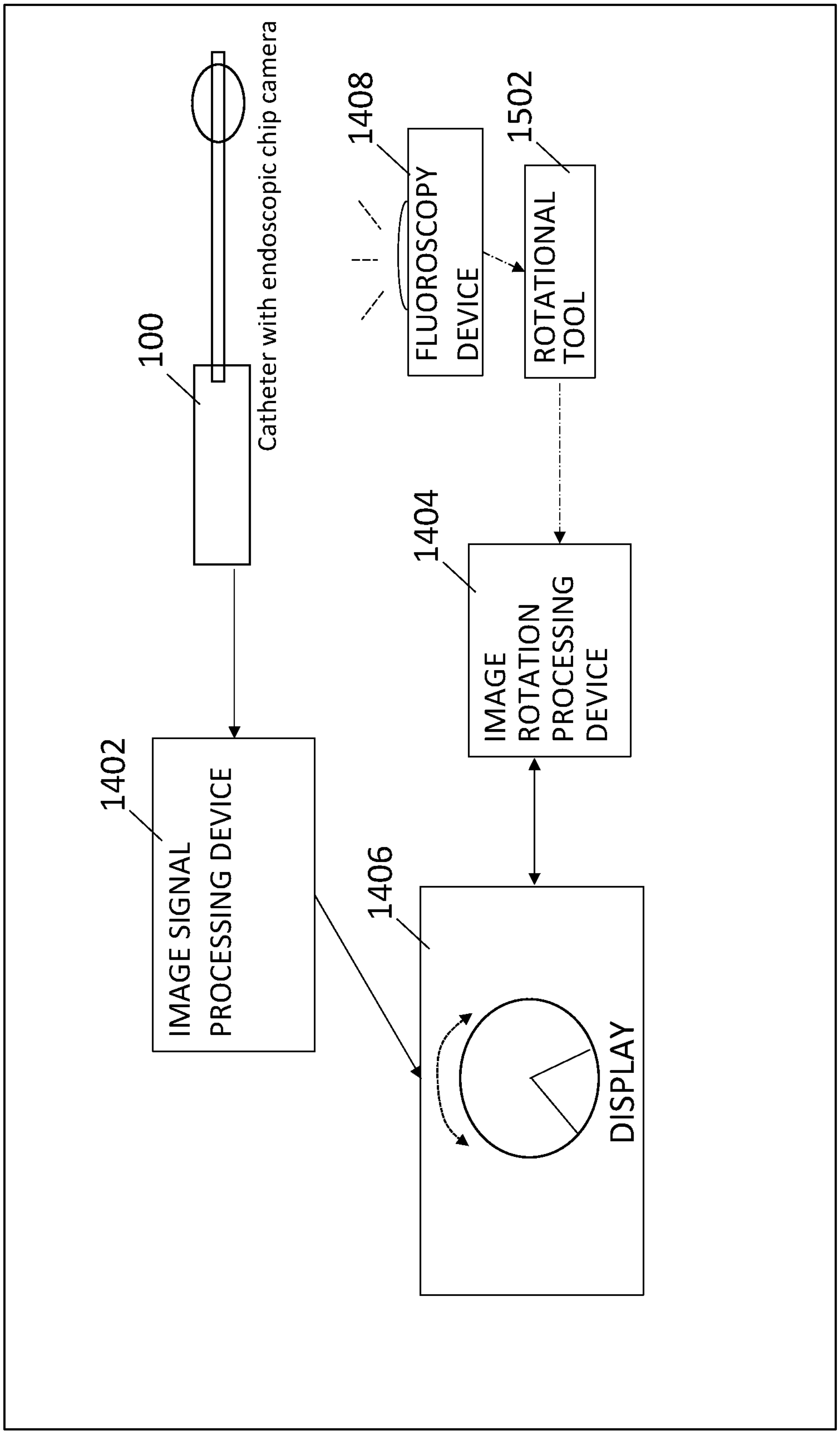
Figure 15A:
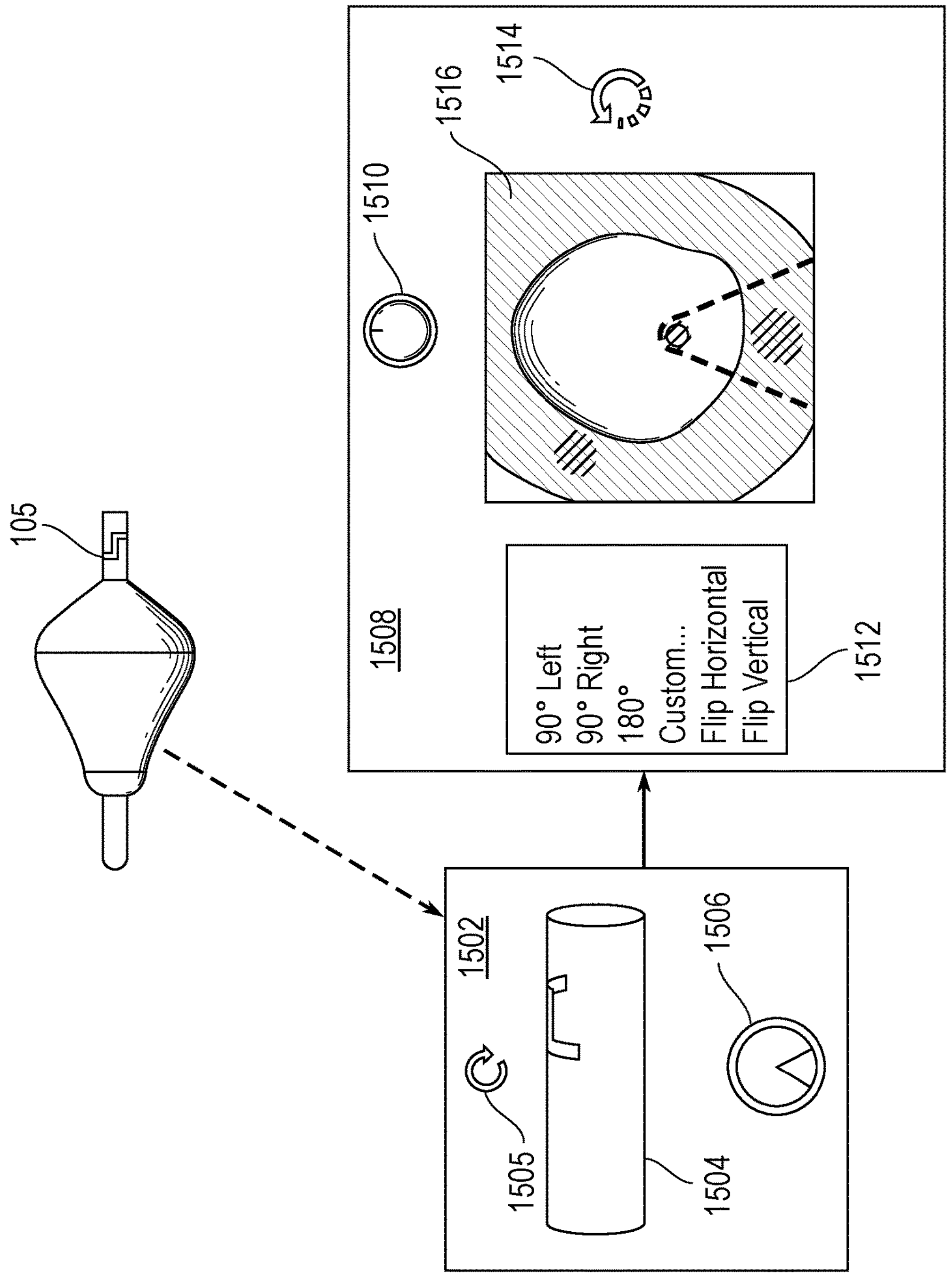
Figure 15B:
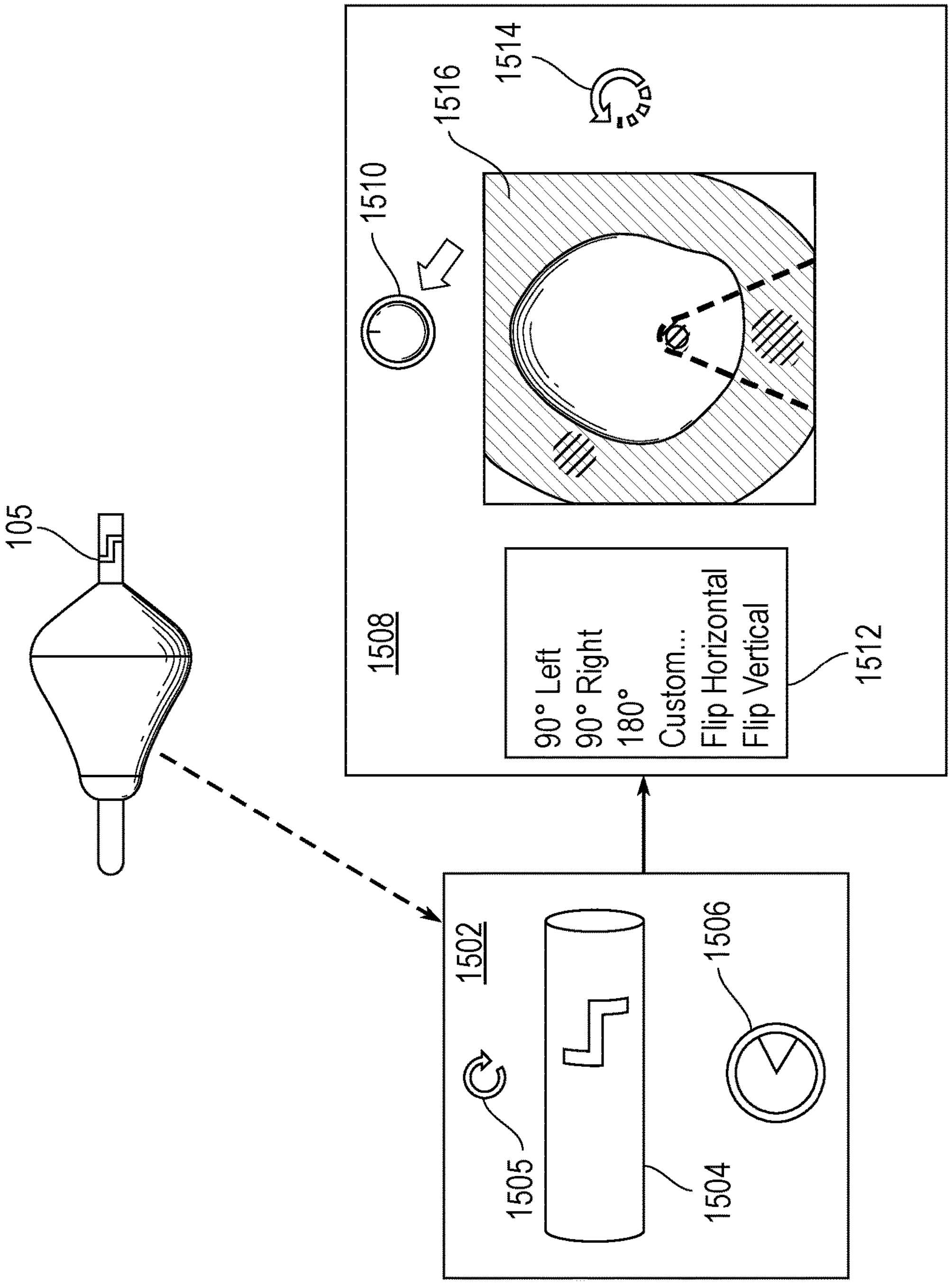
Figure 15C:
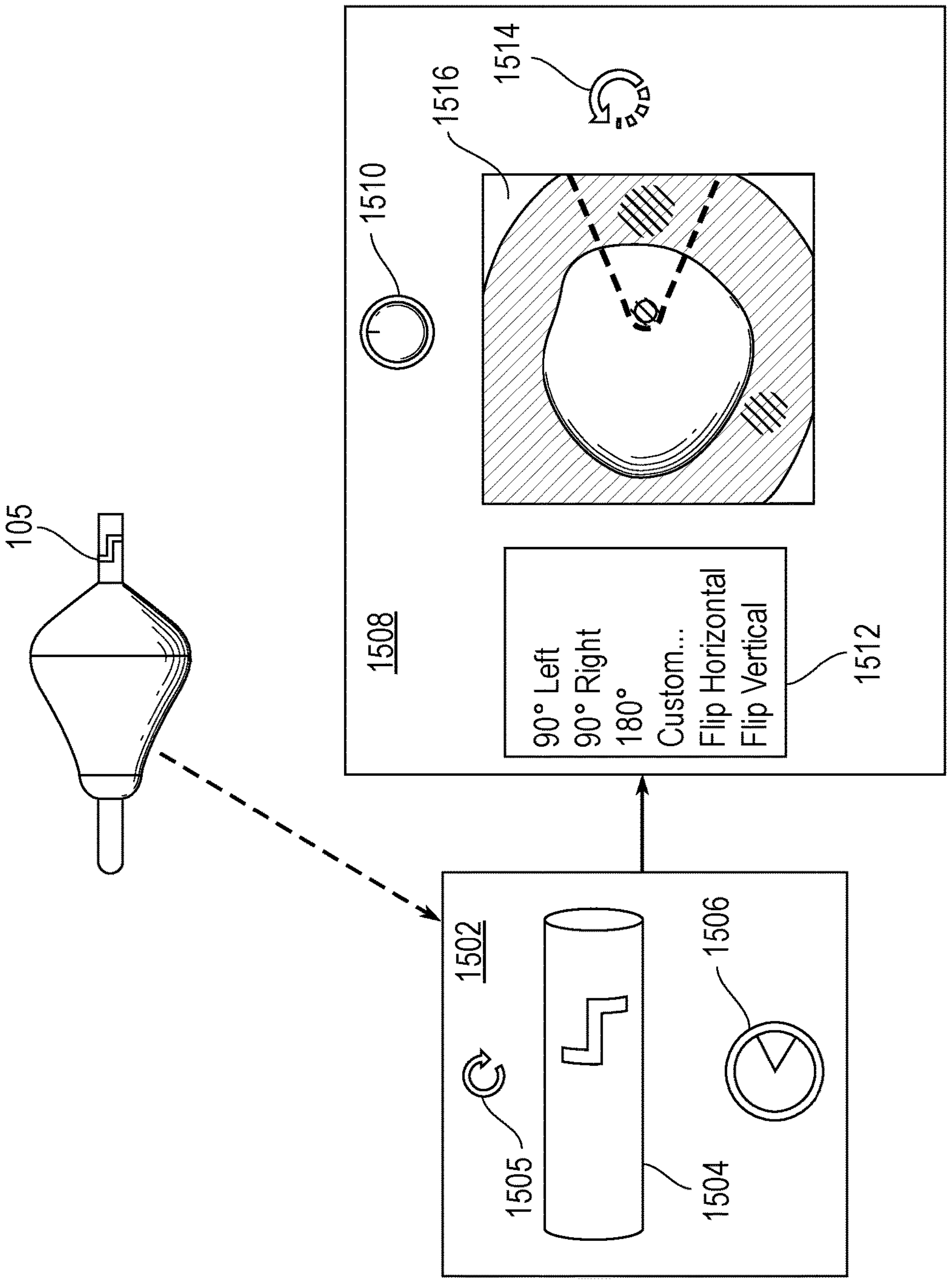
Figure 16:
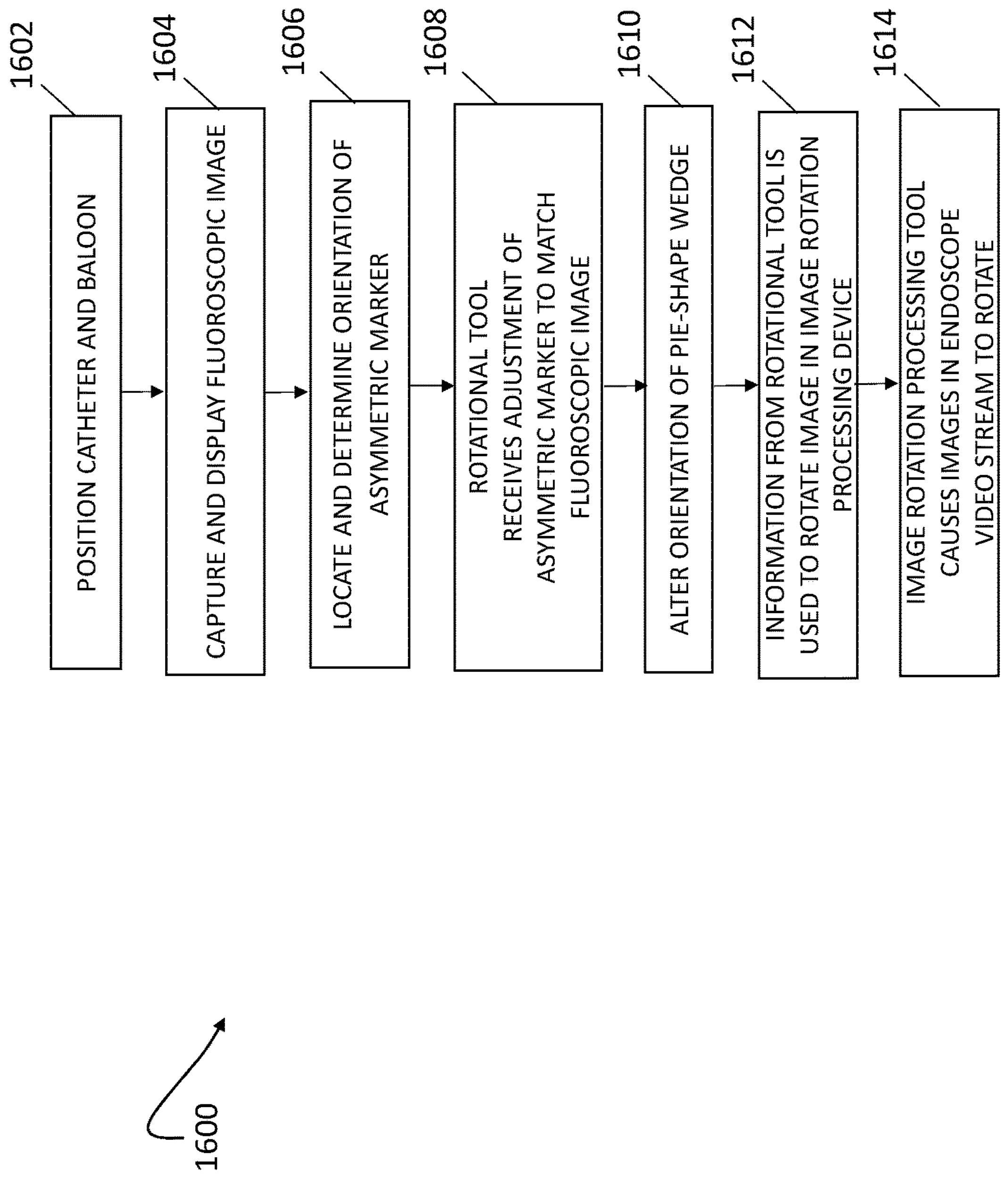

FIGS. 4A-4D are views of the balloon and asymmetric marker with various rotations of the balloon relative to the patient's anatomy and in particular, FIG. 4A shows the balloon and asymmetric marker in the superior position; FIG. 4B shows the balloon and asymmetric marker in the anterior position; FIG. 4C shows the balloon and asymmetric marker in the inferior position; and FIG. 4D shows the balloon and asymmetric marker in the posterior position;

FIGS. 5A-5D are schematic views of endoscopic images (e.g., live feed) with orientations of the pie-wedge shaped regions which correspond to the asymmetric marker anatomical orientations of FIGS. 4A-4D and in particular, FIG. 5A shows a superior position; FIG. 5B shows the anterior position; FIG. 5C shows the inferior position; and FIG. 5D shows the posterior position;

FIG. 6 is a cross-sectional view of a balloon catheter according to a first embodiment and including two forward-facing imaging devices (e.g., two forward-facing imaging chip endoscopes);

FIG. 7A is an image from an example video stream captured by a first forward-facing imaging chip endoscope (e.g., a "left" imaging chip endoscope) and FIG. 7B is an image from an example video stream showing an opposite view from a second forward facing imaging chip endoscope (e.g., a "right" imaging chip endoscope);

FIG. 8A is another image showing the view from the first forward facing imaging chip endoscope and FIG. 8B is another image showing the view from the second forward-facing imaging chip endoscope. As illustrated in FIGS. 8A and 8B, an aiming beam is partially behind the obscured portion of the image for the second forward-facing imaging chip endoscope (FIG. 8B), but the same aiming beam remains fully visible in the first forward-facing imaging chip endoscope (FIG. 8A);

FIGS. 9A and 9B correspond to the images of FIGS. 8A and 8B that have been rotated a prescribed number of degrees to position the superior aspect of the target tissue at the top of each of the images shown in FIGS. 9A and 9B;

FIGS. 9C and 9D correspond to the images of FIGS. 8A and 8B that have been rotated together as a single image a prescribed number of degrees to position the superior aspect of the target tissue at the top of each of the images shown in FIGS. 9C and 9D;

FIG. 10 is a cross-sectional view of a balloon catheter according to a second embodiment and including one forward-facing imaging device (e.g., forward-facing imaging chip endoscope) and a side-facing imaging device (e.g., side-facing imaging device);

FIG. 11A is an image showing the view from the forward facing imaging chip endoscope) of FIG. 10 and FIG. 11B is an image showing the side-facing imaging device of FIG. 9;

FIG. 12 is a cross-sectional view of the balloon catheter according to the second embodiment in which the aiming beam is directed at a location that is diametrically opposite from the forward-facing imaging device with respect to the central shaft of the catheter;

FIG. 13A is an image showing the view from the forward facing imaging chip endoscope) of FIG. 12 and FIG. 13B is an image showing the side-facing imaging device of FIG. 12;

FIG. 14 is a system diagram that includes the catheter with endoscopic chip camera(s), an image signal processing device, an image rotation processing device, and a display device;

FIGS. 15A, 15B, and 15C illustrate three states of use of an example rotational tool and an example graphical user interface that can be provided with the image rotation processing device; and FIG. 16 is a flow diagram showing a routine that illustrates a broad aspect of a method for adjusting orientation of images shown in a graphical user interface.

DETAILED DESCRIPTION OF CERTAIN EMBODIMENTS

Balloon Catheter

Figure 1:
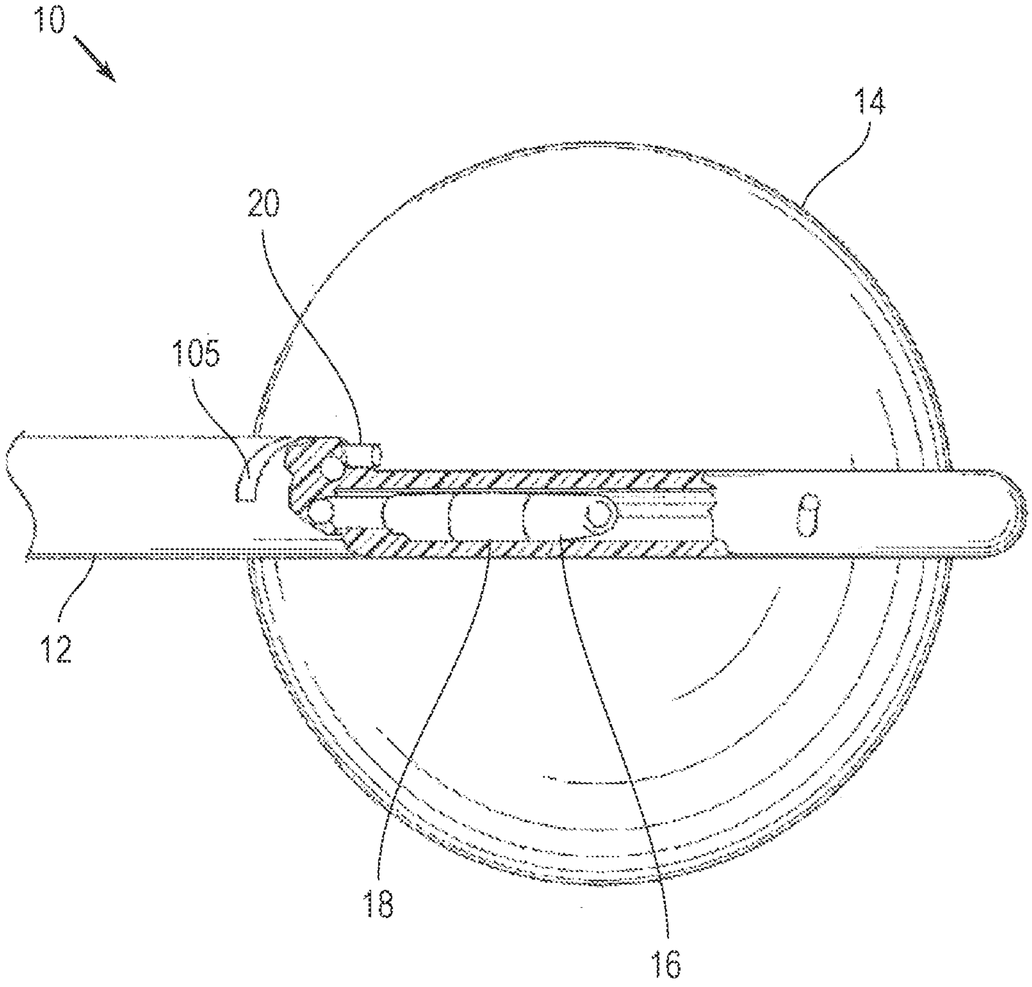
(PRIOR ART) Fig. 1
FIG. 1 is a side view of a conventional ablation catheter with a single endoscope.

FIG. 1 illustrates a traditional balloon catheter 10 for ablating target tissue. The balloon catheter 10 includes an elongate body 12 and a compliant balloon 14 inflatable. A central tubing 16 can also house an energy emitter 18 that is capable of both axial movement and rotation within the tubing. Within the elongated body (also referred to herein as the catheter body) there can be a plurality of additional lumens, through which certain devices or instruments can been passed. The catheter body can carry a marker to assist the clinician in proper placement of the device, e.g., a radiopaque marker (e.g., asymmetric marker 105 in FIG. 3) to aid in fluoroscopic detection. As is known, fluoroscopy is a type of medical imaging that shows a continuous X-ray image on a monitor.

The balloon catheter 10 also has an endoscope 20. As illustrated, the endoscope 20 is forward-facing and is disposed adjacent the central tubing 16. The central tubing 16 is typically formed of a transparent polymer material. The energy emitter 18 is both axially and rotationally movable within the central tubing 16 and thus, the energy emitter 18 is typically located forward of the endoscope 20. As used herein, the term forward-facing refers to the view of the endoscope in a distal direction relative to the catheter body. Similarly, the term side-facing refers to the view of the endoscope in a direction that is radially outward from a side of the catheter body.

Anatomically, locations along the target area can be described in terms of being superior, inferior, anterior or posterior. As is known, anatomically, the term superior describes a location that is toward the head end of the body; the term inferior describes a location that is away from the head; the term anterior refers to the front and the term posterior refers to the back.

In one embodiment, the target tissue is a pulmonary vein. As is known, the pulmonary veins are the veins that transfer oxygenated blood from the lungs to the heart. The largest pulmonary veins are the four main pulmonary veins, two from each lung that drain into the left atrium of the heart. Pulmonary vein isolation is a procedure to treat an abnormal heart rhythm called atrial fibrillation. As mentioned, pulmonary vein isolation is a type of cardiac ablation that uses heat or cold energy to create scars in the heart to block abnormal electrical signals and restore a normal heartbeat. In pulmonary vein isolation, the scars are created in the left upper chamber of your heart in the areas where the four pulmonary veins connect to the left atrium. Right pulmonary veins carry blood from the right lung into the left atrium of the heart and left pulmonary veins carry blood from the left lung into the left atrium.

When the balloon catheter 10 is placed in the body, the rotational orientation of the catheter 10 is random. Consequently, the orientation of the pulmonary vein anatomy (target tissue) as it is visualized by the endoscope 20 and then displayed on the video display screen which can be part of a console or a computing device is also random. This is not desirable. What is desired is to have the orientation of the target tissue, such as the pulmonary vein anatomy appear, on the video display screen in an orientation that displays the superior aspect of the vein at the top of the screen. When so oriented it then follows that the inferior aspect of the vein will be at the bottom of the screen and the posterior aspect of the vein will be on the left side of the screen for the left pulmonary veins and the posterior aspect of the vein will be on the right side the screen for right pulmonary veins.

Having this anatomically correct orientation of the vein on the video display is important for a number of reasons. One reason is that the veins tend to be thinner on the posterior aspect and thicker on their anterior aspect. Consequently, sometimes it is desirable to adjust the laser dose levels when ablating the veins in a manner such that the anterior portions of the vein receive a higher dose and the posterior portion of the veins receive a lower dose. Additionally, the esophagus is generally in close apposition to the posterior portion of the left atrium and sometimes directly behind either the left or right pulmonary veins. Therefore, special precautions such as monitoring the temperature of the esophagus using a temperature monitoring catheter placed in the lumen of the esophagus are desirable when ablating the posterior portion of the veins. Another reason it is important to know the anatomical orientation of the vein on the video image has to do with checking the veins for electrical isolation after the veins have been ablated. The checking for electrical isolation is generally done with a multi-electrode catheter placed in the vein. The position of the multi-electrode catheter is visualized using fluoroscopy. It is sometimes determined that a portion of the vein is not isolated and needs to be re-ablated. The fluoroscopic image of the electrodes on the multi-electrode allow the electrophysiologist to determine the anatomical location of the portion of the vein that is not isolated. Once the endoscopic laser ablation catheter is placed back in the vein it is necessary to properly orient the endoscopic view to the patient's anatomy in order to re-ablate the correct region of the vein that was found to not be isolated using the multi-electrode catheter.

As illustrated in the figures, the present disclosure is directed to a balloon catheter 100 and catheter system that offer a number of improvements over the traditional catheter 10 described above. Both balloon catheters 10, 100 can be thought of as being, in at least one embodiment, a laser ablation balloon catheter that is configured to emit laser energy to ablate tissue.

For example, there are at least three significant improvements (three features) to the balloon catheter 10 of the '066 patent and the '961 patent that make up the present balloon catheter 100.

Referring to FIG. 6, the balloon catheter 100 is similar to the balloon catheter 10 and therefore includes many of the same components which are described herein. For example, the balloon catheter 100 includes an elongate body 102 and an inflatable compliant balloon 125 that surrounds the elongate body 102. The elongate body 102 includes a central tubing 110 that can also house an energy emitter 120 that is capable of both axial movement and rotation within the tubing. Within the elongated body (also referred to herein as the catheter body) there can be a plurality of additional lumens, through which certain devices or instruments can been passed. The catheter body can carry a marker to assist the clinician in proper placement of the device, e.g., a radiopaque marker to aid in fluoroscopic detection.

The balloon catheter 100 includes at least one imaging device 130 and can include a plurality of imaging devices 130, 140 (e.g., two imaging devices). Broadly speaking, each imaging device 130, 140 is configured to generate images (e.g., for a video stream) of the inside of the patient's body that then can be shown on a display device. One common imaging device is an endoscope. As is known, an endoscope is a long, thin, flexible tube that has a light and camera at one end for capturing images of the inside of the patient's body which then displayed on a display device.

The first improvement over the mentioned traditional devices is to replace the reusable fiber-optic endoscope 20 described in Melsky et al U.S. Pat. No. 9,421,066B2 and Melsky et al U.S. Pat. No. 9,033,961B2 with first imaging device 130 in the form of a first miniature imaging chip. The first miniature imaging chip can be in the form of a CMOS or CCD image sensor. An image sensor is broadly speaking a sensor that detects and conveys information used to make an image. The two main types of electronic image sensors are the charge-coupled device (CCD) and the active-pixel sensor (CMOS sensor).

There are several advantages to doing this. First, miniature imaging chips that have recently become available are low enough in cost that they can be incorporated into the balloon catheter 100 as in integral part of the balloon catheter 100 and can be disposed of after the catheter 100 has been used to treat a patient. Conventional fiber-optic endoscopes employed expensive fiber-optic image bundles making the endoscope too costly to be incorporated into a single-use catheter, thereby requiring the catheter 10 to be a reusable device. Conventional endoscopes used in endoscopically guided laser ablation catheters were separate devices that needed to be installed into the catheter 10 before it was used, removed from the catheter 10 after use and then cleaned and re-sterilized for additional uses.

Accordingly, the first imaging device 130 in the form of a first miniature imaging chip can be positioned at the same or similar location as the endoscope 20 that was used in the catheter 10. In other words, the first imaging device 130 is forward-facing and is disposed adjacent the central tubing 110. The central tubing 110 is typically formed of a transparent polymer material. The energy emitter 120 is both axially and rotationally movable within the central tubing 110 and thus, the energy emitter 120 is typically located forward of the first imaging device 130 (e.g., first miniature imaging chip). In addition, the transparent polymer central tubing 110 is located forward of the first imaging device 130.

The first imaging device 130 has a field of view that can be between 90 degrees and 130 degrees. In FIG. 6, the field of view of the first imaging device 130 is indicated by the broken lines identified at 131.

The second improvement is to provide the second imaging device 140 as part of the balloon catheter 100. In order to understand the advantage of using a second imaging chip (second imaging device 140), FIG. 1 of Melsky et al U.S. Pat. No. 9,033,961B2 is reproduced as FIG. 1. FIG. 1 shows the preferred location of the endoscope 20 relative to the energy emitter 18. The energy emitter 18 resides inside the central lumen of the catheter 10 while the endoscope resides outside of lumen and is oriented so that it provides a view generally along the axis of the catheter looking toward the distal end of the catheter 10. As described in Melsky et al U.S. Pat. No. 9,033,961B2, the endoscope position in the catheter 10 is fixed while the energy emitter 18 can translate and rotate in lumen in order that laser energy may be directed to the desired location. Because the energy emitter 18 lies generally forward of the endoscope 20, a portion of the view from the endoscope 20 is obscured by the energy emitter 18. The image is also distorted by the transparent polymer of the central shaft of the catheter 10. This latter distortion happens because transparent polymers suitable for catheter construction invariably have an index of refraction that differs from water, saline, deuterium oxide or other liquids suitable for filling the balloon and this difference in index of refraction causes light to refract, distorting the image seen looking through the central shaft by the endoscope 20.

Figure 2B:
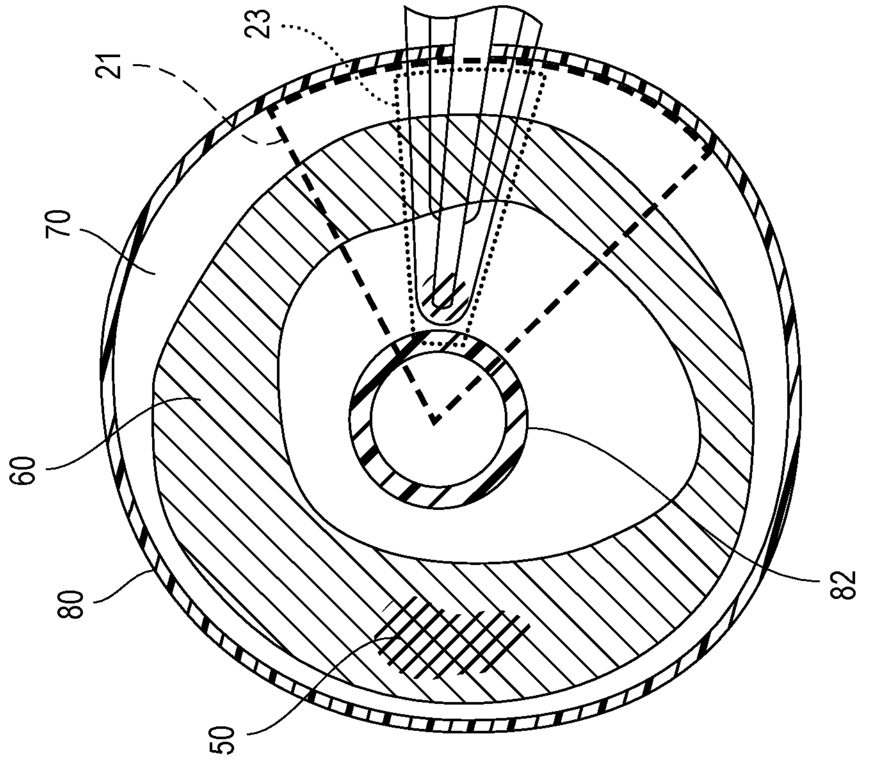
FIGS. 2A and 2B are images showing forward views of the endoscope of the catheter of FIG. 1 showing obstructed view areas caused by the presence of the transparent polymer catheter body itself and the energy emitter when the catheter is placed in the pulmonary vein of a patient.
Figure 2A:
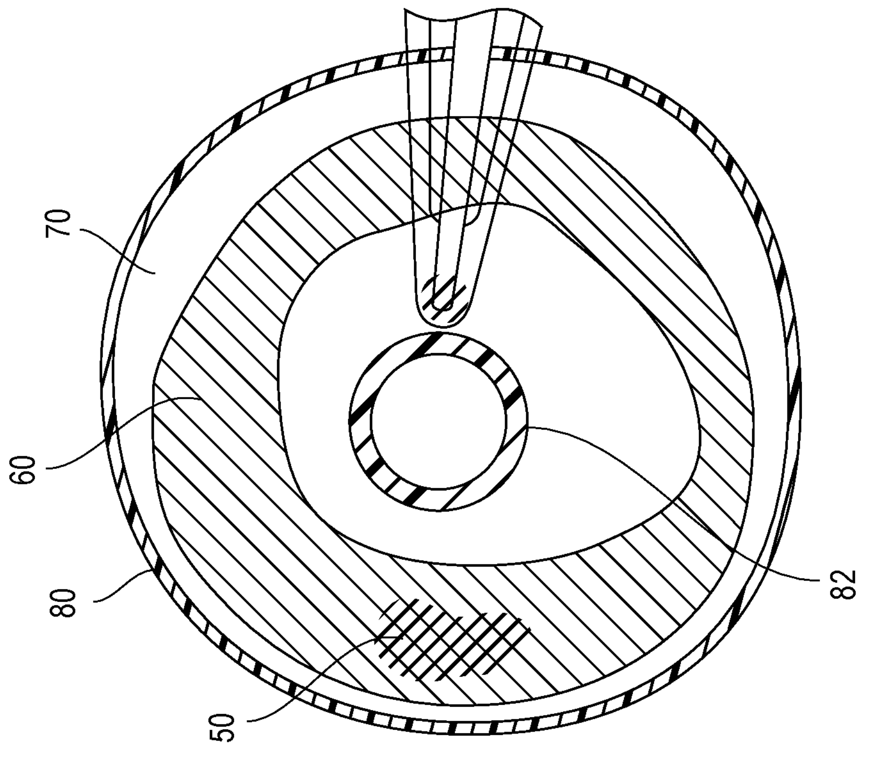

This distortion is illustrated in FIG. 2A which is an image of the view form the endoscope 20 while the catheter 10 is in a patient. As can be seen the endoscopic view of the pulmonary vein is partially obscured by the energy emitter 18 (FIG. 1) and the view is distorted by the clear polymer material surrounding the central lumen of the catheter 10. FIG. 2B shows the same endoscopic view as FIG. 2A but with that portion of the endoscopic view obscured by the transparent polymer of central shaft through which the central lumen passes being outlined in a first dashed line 21 and that portion of endoscopic view obscured by the energy emitter 18 outlined in a second dashed line 23. In the present figures, the first dashed line 21 defines a first region of obstruction (first blind zone) that is due to the transparent polymer catheter shaft and the second dashed line 23 defines a second region of obstruction due to the energy emitter. The area defined by the second dashed line 23 lies within the larger area defined by the first dashed line 21. The first dashed line 21 can be thought of as defining a pie-wedge shaped region as shown in the figures. Thus, as used herein, the term pie-wedge or pie-wedge shape or pie-wedge shaped region refers to an area similar to the area defined by first dashed line 21 that represents an obstruction region or zone or blind spot in which the tissue landscape is not clearly visible in the real-time video stream.

Also, of interest in FIGS. 2A and 2B is a bright spot 50 (often green color) at generally the nine o'clock position in the generally circular endoscopic image. This bright spot 50 is an aiming beam which illuminates the location where the energy emitter 18 is aiming. This is the same location where ablative laser energy will be delivered when the infrared ablation laser is activated. Additionally, we see pulmonary vein tissue in contact with the catheters distal balloon. In an example implementation, on a color display device this tissue appears white or light pink and is generally indicated at 60. On a color display device, red regions generally in the center endoscopic image and at the outer margin of the image are visible and are generally indicated at 70. These regions 70 represent areas where blood is contacting the balloon. The blood in the center of the endoscopic image is blood which is in the lumen of the pulmonary vein distal to the balloon. The blood at the outer margin of the endoscopic image is blood in the left atrium proximal to the balloon. Additionally, in the image we see a white line, generally indicated at 80, near the outer margin of the endoscopic image which has been applied to the surface of the balloon. This white line 80 acts as a visual reference for the user. The white line 80 indicates the location of the maximum diameter of the balloon and is therefore a boundary between the distal, generally forward facing portion of the balloon and the proximal, rearward facing portion of the balloon. There is also a distal white line on the surface of the balloon that appears as a small white circle 82 in the center of the image. This distal white line marks the distal limit of the portion of the balloon suitable for delivering ablative laser energy through.

The obscured and distorted region (the pie-shaped area within the line 21) of the image so described and illustrated in FIG. 2B is not desirable. The reason it is not desirable is because the reason for providing the user with an endoscopic image is to allow the user to be able to appropriately adjust the location of the lesion generator such that the aiming beam 50 is illuminating tissue so that ablative laser energy is delivered into tissue. Additionally, it is desired that ablative laser energy is delivered in such a manner that a continuous ring of tissue is ablated. Only by ablating a continuous ring of tissue will electrical isolation of the pulmonary vein be achieved. The obscured and distorted region of the endoscopic image creates a region where the location of the aiming beam 50 is not visible and so it cannot be determined if the aiming beam 50 is illuminating tissue or blood. Neither can it be determined if lesions being formed in the obscured region are continuous and that there is no gap in the lesion ring being created. In other words, the surgeon ablating the tissue is left blind in this obstruction region.

In prior art implementations, the obscured region was dealt with by first ablating all of the tissue that was readily visible and not obscured by the energy emitter 18 and central shaft and then rotating the entire catheter 10 while the catheter's balloon was positioned in the pulmonary vein. Since the endoscope 18 is in fixed relation to the catheter 10, rotation of the catheter 10 repositions both the endoscope and the obscured region such that tissue that was formerly obscured now falls at a location that is readily visible. This task of rotationally moving the complete catheter 10 after it has properly been positioned at the target location is less than desirable.

The balloon catheter 100 also includes an asymmetric radiopaque marker 105 on either the catheter shaft 110 or the balloon 125 (preferably on the catheter shaft 110 just behind the balloon 125) whose rotational orientation relative to the patient's anatomy may be determined under fluoroscopic visualization. In other words, after the balloon catheter 100 is positioned relative to the target tissue, a fluoroscopic image (static image) is taken to understand the location of the catheter based on the appearance of the opaque asymmetric marker 105 in the static fluoroscopic view. Details of this asymmetric marker 105 and how it is used to determine the correct orientation of the real time endoscopic view that is displayed on the display (screen) are described herein.

In accordance with the present disclosure, the orientation of the endoscopic image (e,g., live real time video stream) on the display screen can be manipulated based on the pie-wedge shaped region (first dashed line 21) where the view of the pulmonary vein is blocked by the central shaft 110 of the catheter 100 and the laser fiber (energy emitter 120) inside that central shaft. This pie-wedged shaped region will act as a reference point for the user to correctly rotate the endoscopic image as described herein. The correct rotational orientation of the pie-wedge is determined by observing the orientation of the asymmetric marker 105 in the fluoroscopic image and from this observation then determining the anatomically correct orientation of the endoscopic video stream as described herein in more detail.

It is important to note that the anatomical orientation of this pie wedge shaped region (identified by first dashed line 21) is always 180 degrees opposite the anatomical orientation of the asymmetric marker 105 located on the shaft 110 of the catheter just proximal of the balloon 120.

Figure 3:
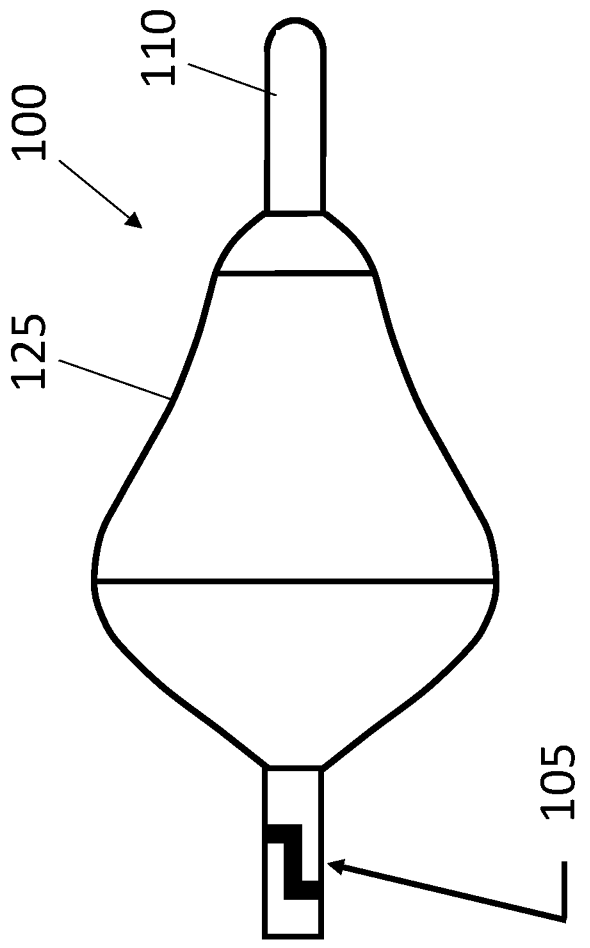
FIG. 3 is a side elevation view of a catheter showing the asymmetric marker.

FIG. 3 shows the asymmetric marker 105 in more detail. It will be appreciated that the illustrated asymmetric marker 105 is only exemplary in nature and other asymmetric markers of different shapes can be used.

Referring to FIGS. 1 and 3, which shows the relationship of the balloon 14 to the central shaft 16 of the catheter 10 and also to the endoscope 20 (e.g., first imaging device 130) and the asymmetric marker 105, it will be appreciated that from the perspective of the endoscope 20, the location of the central catheter shaft 16 is directly below the endoscope 20 and the longitudinal segment of the asymmetric marker 105 is always directly above the endoscope 20. Hence the fact that the anatomical orientation of the pie-wedged shaped region (first dashed line 21 in FIG. 2B) on the endoscopic video is always 180 degrees opposite the anatomical orientation of the asymmetric marker 105 located on the shaft 16 of the catheter just proximal of the balloon 14. It will be understood that these relationships hold true equally for the catheter 100 illustrated herein.

Now referring to FIGS. 4A-4D, the balloon 125 and the asymmetric marker 105 are shown in various orientations with the marker 105 appearing in each of the images as it might appear in fluoroscopy where the polymer catheter shaft 110 material appears relatively transparent while the asymmetric marker 105 is essentially opaque. For FIGS. 4A to 4D, it is important to note that each fluoroscopic image is oriented such that the top of each of FIGS. 4A to 4D would be in the direction of the patient's head or more specifically the top of each of FIGS. 4A to 4D is the superior direction of the patient's anatomy. Also, the plane of each of FIGS. 4A to 4D represents the patient's frontal plane with the fluoroscope looking from the patient's anterior toward the patient's posterior as is commonly employed in cardiac ablation procedures. In each of FIGS. 4A to 4D, the catheter 100 is in a different rotational orientation relative to the patient's anatomy. In each case, the rotational orientation can be determined by observing the location of the longitudinal segment of the asymmetric marker 105. For example, in the image of FIG. 4A, the longitudinal segment of the marker 105 is in the superior direction since it appears on the superior portion of the catheter shaft. Now referring to the corresponding image shown in FIG. 5A, a schematic representation of the endoscopic image that has been correctly rotated to correspond with the patient's anatomy is shown. Since the longitudinal segment of the asymmetric marker 105 in image of FIG. 4A was in the superior direction then the pie shaped region (defined by first dashed line 21) of the endoscopic image is correctly oriented 180 degrees opposite, placing it in the inferior direction. Similarly, images illustrated in FIGS. 4B-4D show the asymmetric marker 105 in the anterior, inferior and posterior directions, respectively, and the images in FIGS. 5B-5D show the corresponding endoscopic images with the correspondingly correct orientations of the pie-wedge shaped region.

Thus, examining the orientation of the asymmetric marker 105 under fluoroscopy allows the user to determine the desired orientation of the pie-wedge shaped region of the endoscopic image such that the superior aspect of the vein is at the top of the display screen of the endoscopic image. Additional details of this aspect of the present disclosure are discussed below.

For this current disclosure, two imaging devices 130, 140 (two imaging chip endoscopes) are used instead of one fiber-optic endoscope 18. The lower cost of the imaging chips makes this economically viable. Additionally, since the imaging chip endoscopes (imaging devices 130, 140) are built into the catheter 100, the time and effort to install two endoscopes into the catheter at the start of the case is avoided. Finally, and most importantly, the imaging chip endoscopes (imaging devices 130, 140) require less room in the proximal portion of the catheter 100 where space is at a premium. The imaging chip endoscopes (imaging devices 130, 140) require approximately 1 mm only for their distal most 3 mm of length whereas the proximal portion of the imaging chip endoscope consists only of wire of less then 0.5 mm in diameter. Therefore, there is room for two imaging chip endoscopes (imaging devices 130, 140) in the catheter 100 of the same dimensions as the prior art catheter 10 that had room for only one fiber-optic endoscope catheter.

FIG. 6 shows a first orientation of the first and second imaging devices 130, 140 in which these two devices 130, 140 are diametrically opposite one another relative to the catheter body. More specifically, the first and second imaging devices 130, 140 can be located 180 degrees apart relative to the catheter body. In the positions illustrated in FIG. 6, the two imaging devices 130, 140 are located rearward of the energy emitter at the same location along the length of catheter body and thus, both of these two devices 130, 140 are forward-facing imaging devices that provide forward looking images. For purposes of the present disclosure, while the term image may be used, it will be appreciated that each of the devices 130, 140 is designed to provide a real-time live video stream of the target tissue and thus, the displayed image on the display is a live video stream in real-time as the ablation procedure is performed.

In this embodiment, the first and second imaging devices 130, 140 can be the same device in that each can be the same type of imaging chip endoscope with the same field of view (e.g., 90 degrees to 130 degrees). As shown in FIG. 6, the field of views of the first and second imaging devices 130, 140 partially overlap as shown in FIG. 6. Both are forward-facing images.

The second imaging device 140 has a field of view that can be between 90 degrees and 130 degrees. In FIG. 6, the field of view of the second imaging device 140 is indicated by the broken lines identified at 141. As discussed herein, what will be appreciated by viewing FIG. 6 is that the first imaging device 130 has its own area of obstruction (blind zone) which is different from the area of obstruction (blind zone) of the second imaging device 140 and in particular is diametrically opposite the area of obstruction of the first imaging device.

FIGS. 7A and 7B show respective images from the balloon catheter 100 incorporating two forward facing imaging chip endoscopes (e.g., from the imaging devices 130, 140) that form part of the catheter 100. For purpose of illustration, FIG. 7A can be considered to be an image from a video stream captured from a left camera (the first imaging device 130) and FIG. 7B can be considered to be an image from a video stream captured from a right camera (the second imaging device 140). The images in FIGS. 7A and 7B show respective angles of view of the same pulmonary vein. The aiming beam 50 can be seen at the six o'clock position. The obscured area for the first imaging device 130 ("left imaging chip endoscope") (labeled left camera) is in the 3 o'clock position of the left hand image of FIG. 7A. The obscured area for the second imaging device 140 ("right imaging chip endoscope") (labeled right camera) is in the 9 o'clock position of the right hand image of FIG. 7B. The aiming beam 50 is shown in these figures and, moreover, the dashed lines 21 in each of FIGS. 7A and 7B indicates an obstruction area or region (blind zone) where the user cannot clearly see the tissue landscape and/or the aiming beam 50 and the location at which the ablative energy (laser energy) is delivered along the tissue.

FIGS. 8A and 8B are views of the same pulmonary vein by the same catheter 100 with two forward facing imaging chip endoscopes (the imaging devices 130, 140). In these images, the aiming beam 50 location has been rotated about 45 degrees clockwise from its previous place shown in FIGS. 7A and 7B, respectively.

So, from FIGS. 7A, 7B, 8A and 8B, it is readily apparent that the use of the two forward-facing imaging chip endoscopes (imaging devices 130, 140) provides the user a field of view of the pulmonary vein that is not obscured at any point around the circumference of the vein while keeping the basic architecture of the prior art catheter intact.

A second embodiment of the invention shown in FIG. 10 also uses two imaging chip endoscopes 130, 140 and the object of this second embodiment, like the first embodiment, is in part to eliminate the obscured region of the pulmonary vein present in the prior art catheter 10. As discussed below, the difference between the first and second embodiments is the location of the second imaging device 140.

In the second embodiment illustrated in FIG. 10, the first imaging device 130 (first imaging chip endoscope) is located where the fiber-optic endoscope 18 is located in the prior art catheter 10 (i.e., along the catheter tube rearward from the energy emitter). The second imaging device 140 (second imaging chip endoscope) is attached to the distal end of the energy emitter 120 and moves with the energy emitter 120. The second imaging device 140 is aimed so that the aiming beam spot 50 is at or toward the center of the field of view of the second imaging device 140. Since the second imaging device 140 is always forward of the energy emitter 120, its view of the pulmonary vein anatomy is never obscured by the energy emitter 120. Additionally, the orientation of the second imaging device 140 relative to the clear polymer material comprising the central shaft 110 of the catheter 100 is such that optical distortions caused by the clear polymer material are minimized. This is because the light rays which form the image of the pulmonary vein anatomy pass through the clear polymer material at angles that are substantially normal to the material and all the rays pass through clear polymer material that is substantially of uniform thickness. In other words, the second imaging device 140 can be considered to be a side-facing imaging chip endoscope in contrast to the first imaging device 130 which is a forward-facing imaging chip.

However, because this second imaging chip endoscope images only a segment of the pulmonary vein anatomy it would be difficult for the user to appreciate the full nature of the pulmonary vein anatomy and to plan an appropriate path for ablative laser energy application in order to electrically isolate the vein. To overcome this drawback, the image from the first forward-facing imaging chip endoscope (first imaging device 130) is available to the user in addition to that of the second side-facing endoscope (second imaging device 140).

FIG. 10 shows, in cross section, the distal balloon end of the catheter with the balloon 125 residing in a pulmonary vein. Everything which contacts the surface of the balloon 125 and falls within the acute angle of this first set of field of view lines 131 is visible to the first imaging device 130 (first imaging chip endoscope) (excepting for areas obscured or distorted by the energy emitter or the central shaft of the catheter as described above). The second side-facing imaging chip endoscope (second imaging device 140) resides on the forward end of the energy emitter 120.

A second set of dashed lines 141 is shown which indicate the field of view of this second side-facing endoscope (second imaging device 140). Also shown in FIG. 10 is the aiming beam 50 emanating from the energy emitter 120 with the dashed lines representing the scope of the aiming beam 50.

Since the second imaging device 140 (the second imaging chip endoscope) is attached to the energy emitter 120, it will translate and rotate with the energy emitter 120. As the second imaging device 140 (the second imaging chip endoscope) translates and rotates, the field of view of the second imaging device 140 translates and rotates as well. As is apparent from FIG. 10, there are locations on the surface of the balloon 125 where pulmonary vein tissue is in contact with the balloon 125 and is therefore a potential target for receiving ablative laser energy but, some of these locations are not visible to the forward-facing first imaging device 130. These locations are either outside the field of view of the first imaging device 130 or they are obscured by the energy emitter 120 or distorted by the central shaft 110 of the catheter 100. Also apparent from FIG. 10 is that these locations while not visible to the first imaging device 130 (first imaging chip endoscope) are perfectly visible to the side-facing second imaging device 140. In particular, note how in FIG. 10 the aiming beam 50 (which can be green light), while illuminating tissue at an ideal location for ablation is unfortunately only partially visible to the first imaging device 130. More specifically, the field of view of the aiming beam 50 is not entirely contained within the field of view of the first imaging device 130.

If the only view available was that of the first imaging device 130, ablation in this location would not be advisable since the user would not be able to determine if the area of the balloon 125 outside the field of view of the first imaging device 130 was actually in contact with tissue. If the area of the balloon 125 outside of the field of view of the first imaging device 130 were in contact with blood, then ablation would not create an adequate lesion to facilitate electrical isolation and may even represent a risk to patient since large amounts of laser energy delivered directly into blood represent a thromboembolic risk should the blood receive enough laser energy that a thermal coagulation of the blood is induced. However, since a view from the side-facing second imaging device 140 is available as a component of the catheter 100 of the present disclosure, the region of the balloon 125 surrounding the aiming beam 50 is fully visualized and ablation can proceed, guided by the view from the side-facing second imaging device 140 without the need to adjust the balloon 125 position in order to compensate for the field of view of the first imaging device 130 not fully capturing the area of tissue contacting the balloon 125.

FIGS. 11A and 11B show the two endoscopic views provided by the two imaging device 130, 140 (two imaging chip endoscopes) in FIG. 10. FIG. 11A is the endoscopic view from the first imaging device 130 and FIG. 11B is the endoscopic view from the second imaging device 140.

FIG. 11A shows the circular ring of pulmonary vein tissue contacting the balloon 125 that users are accustomed to seeing in the prior art catheter 10 with a single forward-facing endoscope 20. The (green) aiming beam 50 is partially visible at the 12 o'clock position in FIG. 11A but only the distal portion of the aiming beam 50 is visible to the forward-facing first imaging device 130. FIG. 11B shows the view from the side-facing second imaging device 140. Whereas the forward-facing first imaging device 130 gives the user an appreciation of the generally circular area of contact of the balloon with the pulmonary vein, some regions of contact are not visible because of limitations of the field of view of the first imaging device 130. The side-facing second imaging device 140 augments the view from the forward-facing first imaging device 130, thereby providing a clear view of the (green) aiming beam 50, the tissue it is illuminating and the surrounding region and allowing ablation to be performed in this region where it would not otherwise be able to be performed without some adjustment of the position of the balloon 125.

With reference now to FIG. 12, the energy emitter 120 and the second imaging device 140 has been rotated relative to their positions in FIG. 10. As previously mentioned, the first imaging device 130 remains at a fixed location once the balloon catheter 100 is anchored at its target location relative to the pulmonary vein ("PV") or other target location. It will be appreciated that in FIG. 12, the aiming beam 50 would be partially or entirely obscured by the energy emitter 120 and central shaft of the balloon catheter 100 when it is viewed by the forward facing first imaging device 130. The images from both the first and second imaging devices 130, 140 resulting from the configuration shown in FIG. 12 is shown in FIGS. 13A and 13B.

FIGS. 13A and 13B illustrate the situation in which the aiming beam 50 is almost entirely obscured by the energy emitter 120 in FIG. 13A from the forward-facing first imaging device 130. However, the aiming beam 50 and surrounding tissue are perfectly visible in the image from the side-facing second imaging device 140, thereby allowing ablation to be performed in this region where it would not otherwise be able to be performed with the prior art catheter 10 (that only included the single endoscope 20) without rotating the entire catheter 10 to bring the obscured area into view of the forward-facing first imaging device 130.

As with FIG. 10, the field of view of the first imaging device 130 is shown at 131, the field of view of the second imaging device 140 is shown at 141 and the scope (illumination area) of the energy emitter is shown at 50 and is indicated in heavier dashed lines compared to the dashed lines 131, 141.

Orientation of the Target Tissue

As previously mentioned, when viewing endoscopic images, such as those shown in FIGS. 8A and 8B, it will be understood that the superior and anterior locations of the displayed pulmonary vein depend on the orientation of the stationary balloon catheter 100 relative to the pulmonary vein. As mentioned, balloon catheter 100 is advanced to the target location, such as the ostium of a pulmonary vein, and seats against the pulmonary vein in an optimal position defined by the balloon entirely seating against tissue. The location of the forward-facing first imaging device 130 thus depends entirely on the orientation of the balloon catheter 100 relative to the PV tissue. In other words, the superior portion (aspect) of the pulmonary vein is not necessarily shown at the top of the displayed image. In FIGS. 8A and 8B, the superior portion of the imaged pulmonary vein is indicated by the letter S and the anterior portion of the imaged pulmonary vein is indicated by the letter A. As shown in FIGS. 8A and 8B, the superior portion of the pulmonary vein is not located at the top of the image. As shown, in this position of the stationary balloon catheter 100, the superior portion S is located generally between the 7 o'clock location to the 8 o'clock location and the anterior portion A is located generally between the 1 o'clock location to the 2 o'clock location.

When viewing an image on an upright display device, such as a display device that is configured as part of a console or as a standalone unit, the orientation of the image(s) can be particularly important for the surgeon to readily recognize and understand the location of the target tissue as well as the orientation of the surrounding anatomical structures. For example, certain areas of the pulmonary vein interface with surrounding anatomical structure and, thus, ablation in these areas requires increased due care during the ablation process. Any confusion of the user regarding locations of the pulmonary vein interface or surrounding anatomical structures during a procedure can result in patient harm as described previously.

To eliminate or at least reduce confusion that can occur during the surgical procedure, captured images in a video stream shown on a display device can be altered, such to provide uniform orientation and positioning. It will be appreciated that orienting endoscopic images to show the superior aspect of the pulmonary vein located at the 12 o'clock position and, accordingly, the inferior aspect at the 6 o'clock position improves the surgeon's recognition and understanding during an ablation procedure.

FIGS. 9A and 9B illustrate the original images of FIGS. 8A and 8B in a reoriented form to illustrate the superior aspect (S) of the PV being located at the top of the image and the inferior aspect (A) of the PV being located at the bottom of the image. By changing the orientation of the images, the surgeon can immediately comprehend the landscape of the PV, since the superior aspect (S) is located at the top (12 o'clock position) of the displayed image in both FIGS. 9A and 9B. In terms of the anterior and posterior regions of the PV and their locations on the reoriented images of FIGS. 9A and 9B, this will depend on whether the targeted PV being displayed is a left pulmonary vein or a right pulmonary vein. More specifically, for a right pulmonary vein, the anterior region is located on the left side of the reoriented image of FIGS. 9A and 9B (with the posterior region on the right side). Conversely, for a left pulmonary vein, the anterior region is located on the right side of the reoriented image of FIGS. 9A and 9B (with the posterior region on the left side).

FIGS. 9C and 9D show another way to reorient the images of FIGS. 8A and 8B that is different than the manner in which the images are rotated as shown in FIGS. 9A and 9B. Rotating both of the images in FIGS. 8A and 8B together may in certain instances be more desirable since the two images in FIGS. 8A and 8B may be close to one another and perhaps overlapping and merging into a single image with little or none of the pie-wedge shaped obscured area appearing on the merged image. In this type of situation, the user would want to rotate the two images (8A and 8B) together as an ensemble (i.e., as a single divided stream that moves as one ensemble). In the rotation shown in FIGS. 9C and 9D from FIGS. 8A and 8B, it will be appreciated that in FIG. 8A, the left endoscope live feed is on the left, but when the two streams of FIGS. 8A and 8B are rotated together to position the superior location at the top of the image, the left endoscope live feed is shown on the right as FIG. 9D. Similarly, FIG. 8B which originally is on the right is now positioned on the left as FIG. 9C.

It will be appreciated that while, the figures are labeled A and B, the two live streams are displayed on the same display screen and thus can be considered to be a single video stream based on combined images from the two endoscopes.

In practice a total merging of the two images would require either exact camera orientation during manufacture or an adjustment of the electronic images at the start of the procedure so it may be impractical.

Changing the orientation of an image during an ablation procedure requires precision. Too much or too little change in orientation can result in the superior aspect, for example, being offset from the 12 o'clock position and potentially confusing the surgeon. To accommodate the need for precision, proper image rotation can be provided using a rotational tool, which can be configured as a physical tool or a software tool. The rotational tool can include the same shaped asymmetric radiopaque marker that is configured on the catheter shaft or balloon, as well as the same shaped catheter body (shaft). The asymmetric marker 105 that is on the catheter shaft or balloon appears under fluoroscopic visualization and is compared with the corresponding asymmetric marker located on or provided by the rotational tool. For example, the relative rotated position of the asymmetric marker 105 on the catheter shaft or balloon is determined, for example, upon visual inspection of one or more fluoroscopic images. The corresponding asymmetric marker on or provided by the tool is, thereafter, rotated to match the determined relative rotated position determined from the fluoroscopic images. The tool provides the user with information that is usable for re-orienting images in a video stream received from the imaging device(s) during the ablation procedure.

More particularly, by examining the orientation of the asymmetric marker under fluoroscopy the user can determine the desired orientation of the pie-wedge shape region of the endoscopic image(s). Once the desired orientation of the pie-wedge shape region is determined, images in the endoscopic video stream can be re-oriented (e.g., rotated) to ensure the relative positions of aspects, such as the superior aspect of the vein, can be adjusted appropriately. For example, the images can be rotated so that the superior aspect of the vein is oriented at the 12 o'clock position, while the inferior aspect is oriented at the 6 o'clock position, the anterior aspect is provided at the 3 o'clock position and the posterior aspect is provided at the 9 o'clock position.

Referring now to FIG. 14, a system diagram is provided that shows an example arrangement that includes the catheter with endoscopic chip camera(s) 100, image signal processing device 1402, image rotation processing device 1404, and display device 1406. Further, the example devices shown in FIG. 14 include fluoroscopy device 1408 and rotational tool 1502. Although the example in FIG. 14 shows the image signal processing device 1402 and image rotation processing device 1404 as separate devices, it is recognized that devices 1402 and 1404 can be configured in one single processing device.

The devices shown in FIG. 14 can provide for altering the orientation (e.g., rotating) of images from in the endoscopic video stream once the desired rotational orientation has been determined. Solid or dashed line connections between the respective devices can represent transmissions using any known arrangement or technique for sending and receiving information to and from devices.

In the example system shown in FIG. 14, the image signal processing device 1402 can interface with the catheter with endoscopic chip camera(s) 100, including to convert signals from the chip camera(s) 130/140 into a standard video signal, such as an analog NTSC signal or HDMI signal. Alternatively, the image signal processing device 1402 can convert signals received from the chip camera(s) 130/140 into a video stream capable of being transferred to the image rotation processing device 1404 which can be a computer, such as via a USB or other suitable interface. The image rotation processing device 1404 can operate to manipulate images within the video stream to display the images in any rotation on the display device 1406, including as selected by the user.

In one or more embodiments, a graphical user interface can be included with controls for the user to define a desired rotation. For example, a user can cause a clockwise or counterclockwise rotation by tapping a touchscreen device, clicking a mouse or other selector device, turning a virtual or physical knob, pressing a virtual or physical button, or by selecting some other suitable interface control. Further, one or more parameters can be set that defines various properties, such as the direction of rotation and/or predefined increments (or custom amounts) of rotation that are suitable for a respective user. Other implementations are similarly supported and envisioned, such as to provide an interface by which a user makes a selection using a touchscreen, mouse, or other suitable interface gestures (e.g., dragging, swiping, pinching/zooming, or the like), which cause a processor to rotate an image by a particular amount and in a respective direction.

FIGS. 15A, 15B, and 15C illustrate three states of use of an example rotational tool 1502 and an example graphical user interface 1508 that can be provided with image rotation processing device 1404. In the example illustrated rotational tool 1502, a fluoroscopic image is shown that includes asymmetric marker 105 that is currently oriented during an ablation procedure. Rotational tool 1502 can include section 1504, which includes a rotatable asymmetric marker that corresponds in shape to marker 105. As shown, the rotatable asymmetric marker is located along a (virtual or physical) catheter representation and the location of the asymmetric marker on the catheter representation and the relative sizes of the asymmetric marker and catheter representation mirror the catheter and marker shown in the fluoroscopy image. Also shown in example rotational tool 1502 is pie-wedge shape in section 1506, which is correspondingly oriented according to the respective orientation of the marker shown in section 1504. In particular, rotational tool 1502 can include a rotatable graphical control 1505 that, when selected, can be used by the user to rotate the orientation of the asymmetric marker in section 1504 to match the orientation of marker 105 shown in the fluoroscopic image. It will also be appreciated that section 1504 can include other graphical controls that permit different manipulation of the catheter representation that includes the asymmetric marker.

Sections 1504 and 1506 can be presented in different orientations, such as side-by-side or stacked as shown.

FIG. 15B illustrates a second state after which the user has altered the orientation of the asymmetric marker in section 1504 (e.g., via control 1505) to match the orientation of the asymmetric marker 105 represented in the fluoroscopic image. After the adjustment in section 1504 is made, the orientation of the pie-wedge shape in section 1506 correspondingly adjusts. In other words, as the user alters the orientation of the asymmetric marker in section 1504, the position of the pie-wedge shape in section 1506 rotates automatically.

As can be seen from the third state shown in FIG. 15C, after the orientation of the pie-wedge shape in section 1506 is adjusted, one or more graphical screen controls can be used to alter the orientation of the pie-wedge shape in section 1516. For example, rotational knob 1510 can be rotated by the user using a mouse, touchscreen, or other suitable device to adjust the orientation of the pie-wedge shape in section 1516. Other controls include menu section 1512 that includes selectable options rotating the pie-wedge shape by various preset or custom amounts, as well rotate button 1514 that, when selected, causes the pie-wedge shape to rotate by a predetermined amount. Thus, as shown and described herein, the correct rotational orientation of the pie-wedge shape in section 1516 can be determined by observing the orientation of the asymmetric marker 105 in the fluoroscopic image. Using the observed orientation, orientation adjustments can be made to a corresponding asymmetric marker in rotation tool 1502, which results in an altered orientation to pie-wedge shape in section 1506. The altered orientation of pie-wedge shape in section 1506 can, thereafter, be used to alter a corresponding pie-wedge shape in section 1516 in graphical user interface 1508, which results in automatically altering orientation of images in the endoscopic video stream.

Although the example shown and described with regard to FIGS. 15A-15C include graphical screen controls for user interactions, automatic processes can be supported, thereby eliminating a need for user input. In certain embodiments, automatic processing of an image can occur for adjusting or altering the orientation of the orientation of the asymmetric marker and/or the pie-wedge shape without requiring user input. For example, machine learning and artificial intelligence can be provided for a computing device to recognize the orientation of the asymmetric marker 105 or the pie-wedge shape and to alter the orientation of an image to ensure that a respective aspect is positioned appropriately (e.g., at the 12 o'clock position). Training can include processing images for identifying various orientations, which can be confirmed or corrected automatically, with user input, or by some combination thereof. After training has occurred and, for example, during an ablation procedure, a computing device that is configured with or as part of an endoscope can recognize respective orientation(s) represented in an image received from one or more devices. A computing device can automatically alter the orientation or rotation of, for example, the asymmetric marker or pie-wedge shape to ensure the aspects are at predefined positions, such as the 12 o'clock and 6 o'clock positions. Other suitable techniques for providing or maintaining orientation of an image are further envisioned and supported, which may not require machine learning and artificial intelligence. For example, metadata associated with respective images can be used to identify and alter an image's orientation.

Furthermore, options can be included to provide for a hybrid arrangement of automatic and manual processing to adjust orientation of an image. For example, a computing device can process an image captured by an endoscope automatically to alter the orientation of the image. Thereafter, a user can issue a command, such as by tapping on a touchscreen, making a selection using a mouse or other pointing device, pressing a button or other physical control, or taking some suitable action to override an automatic process and to enable manual processing, such as shown and described herein.

It will be appreciated that while in the above example, each image is oriented such that the superior region of the PV (target tissue) is located at the top of the display, the user can select other orientations to accommodate customized views and uses.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

Turning now to FIG. 16, a flow diagram is described showing a routine 1600 that illustrates a broad aspect of a method for adjusting orientation of images shown in graphical user interface 1508, in accordance with at least one embodiment disclosed herein. It should be appreciated that several of the logical operations described herein are implemented (1) as a sequence of computer implemented acts or program modules running on a communication device and/or (2) as interconnected machine logic circuits or circuit modules within a communication device. The implementation is a matter of choice dependent on the requirements of the device (e.g., size, energy, consumption, performance, etc.). Accordingly, the logical operations described herein are referred to variously as operations, structural devices, acts, or modules. Various of these operations, structural devices, acts and modules can be implemented in software, in firmware, in special purpose digital logic, and any combination thereof. It should also be appreciated that more or fewer operations can be performed than shown in the figures and described herein. These operations can also be performed in a different order than those described herein.

The process begins at step 1602 where the catheter with endoscopic chip camera(s) 100 is positioned. Once positioned, a fluoroscopic image of catheter with endoscopic chip camera, including the asymmetric marker, is captured by and displayed, for example, by fluoroscopy device 1408 (step 1604). Thereafter, the asymmetric marker 105 in the fluoroscopic image is located and the orientation of the marker is determined (step 1606). One or more adjustments are made using the rotational tool 1502 so that the asymmetric marker shown in the rotational tool corresponds to that shown in the fluoroscopic image (step 1608). Thereafter, the orientation of the pie-wedge shape is altered (step 1610). Information from the image rotation tool 1502 is used to rotate an image in the image rotation processing device 1404 (step 1612). For example, controls can be selected by the user to change the orientation of the pie-wedge shape in section 1516 to match that shown in 1506. Thereafter, the image rotation processing device 1404 uses the information associated with the altered pie-wedge shape to cause rotation of the images from the endoscopic video stream (step 1614).

Embodiments of the subject matter and the operations described in this specification can be implemented in digital electronic circuitry, in computer software, firmware, or hardware, including via various known structures and structural equivalents, or in combinations of one or more of them. Embodiments of the subject matter described herein can be implemented as one or more computer programs, i.e., one or more modules of computer program instructions, encoded on computer storage medium for execution by, or to control the operation of image signal processing device 1402 and image rotation processing device 1404. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

In accordance with one or more embodiments, image signal processing device 1402 and/or image rotation processing device 1404 can be configured as one or more forms of digital computers, such as laptops, desktops, workstations, personal digital assistants, servers, blade servers, cellular telephones, smart-phones, mainframes, and other appropriate computers. The components shown and described herein, and their respective functions, are meant to be exemplary only, and are not meant to limit described and/or claimed embodiments.

Further, image signal processing device 1402 and/or image rotation processing device 1404 can include one or more of a processor, a memory, a storage device, a high-speed interface connecting to the memory and multiple high-speed expansion ports, and a low-speed interface connecting to a low-speed expansion port and a storage device. Each of the processor, the memory, the storage device, the high-speed interface, the high-speed expansion ports, and the low-speed interface can be interconnected using various busses and can be mounted on a common motherboard or in other manners as appropriate. The processor can process instructions for execution within the computing device, including instructions stored in the memory or on the storage device to display graphical information for a GUI on an external input/output device, such as a display 1406 coupled to the high-speed interface. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

Moreover, the memory configured with image signal processing device 1402 and/or image rotation processing device 1404 can store information. In one or more embodiments, the memory can be a volatile memory unit or units, or a non-volatile memory unit or units. The memory can also be another form of computer-readable medium, such as a magnetic or optical disk. The storage device is capable of providing mass storage for image signal processing device 1402 and/or image rotation processing device 1404. In some implementations, the storage device can be or contain a computer-readable medium, e.g., a computer-readable storage medium such as a floppy disk device, a hard disk device, an optical disk device, or a tape device, a flash memory or other similar solid state memory device, or an array of devices, including devices in a storage area network or other configurations. A computer program product can also be tangibly embodied in an information carrier. The computer program product can also contain instructions that, when executed, perform one or more methods, such as those described above. The computer program product can also be tangibly embodied in a computer- or machine-readable medium, such as the memory, the storage device, or memory on the processor.

It will be appreciated that the image processing system described above can be used in combination with any of the catheters described herein including the catheter types shown in FIGS. 1, 6, 10 and 12 which include the use of a single endoscope as well as plural endoscopes (e.g., plural imaging chip endoscopes).

The systems and techniques described here can be implemented in a computing system that includes a back end component (e.g., as a data server), or that includes a middleware component (e.g., an application server), or that includes a front end component (e.g., a client computer having a graphical user interface or a web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any implementation or of what may be claimed, but rather as descriptions of features that may be specific to particular embodiments of particular implementations. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The balloon catheter 100 and the associated system thereof offer a number of advantages over traditional balloon catheter systems including but not limited to the following features:

(a) a balloon catheter which may be introduced into the body and positioned in a pulmonary vein with the balloon in contact with the vein ostium;

(b) a side firing laser fiber that is longitudinally and rotationally positionable in the balloon for the purpose of delivering laser energy through the balloon and into the portion of the pulmonary vein in contact with the balloon;

(c) an electronic chip endoscope permanently or replaceably installed in the balloon catheter for the purpose of visualizing at least a portion of the interior of the balloon including at least a portion of the catheter shaft inside the balloon, and capable of discriminating between pulmonary vein tissue in contact with the balloon vs atrial blood in contact with the balloon;

(d) an asymmetric radiopaque marker on either the catheter shaft or the balloon (preferably the catheter shaft just behind the balloon) whose rotational orientation relative to the patient's anatomy may be determined under fluoroscopic visualization; and (e) an image processing system that processes the video signal from the endoscopic chip camera and a display screen that displays the endoscopic video signal such that the rotational orientation of the video image stream may be rotated by the user. The display screen is preferably a touch screen and the means by which the user rotates the image is by interfacing with a touch screen user interface control. The purpose of rotating the video image stream is to orient the video images of the pulmonary vein in contact with the balloon such that their anatomical orientation is known and correct. Correct anatomical orientation will place the superior aspect of the vein at the top of the display screen.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments but should be defined only in accordance with the following claims and their equivalents.

What is claimed is:

1. A computer implemented method for altering an orientation of an endoscopic image received during a surgical procedure, the method comprising:

providing, by at least one computing device configured with a graphical user interface, an image of a catheter configured with a first marker and captured during a surgical procedure, wherein the catheter is in a respective orientation;

providing, by the at least one computing device via the graphical user interface, a second marker that corresponds to the first marker and is rotatable as a function of at least one control included in the graphical user interface, wherein the second marker appears in an orientation that is different than an orientation of the catheter;

altering, by the at least one computing device in response to at least one selection received in the graphical user interface, the orientation of the second marker to match the orientation of the catheter;

automatically providing, by the at least one computing device via the graphical user interface in response to the altered orientation of the second marker, a first shape that represents at least an obstructed portion of the endoscopic image, wherein the first shape is in a respective orientation;

providing, by the at least one computing device via the graphical user interface, a representation of a second shape that is rotatable as a function of at least one control included in the graphical user interface, wherein the second shape appears in an orientation that is different than the orientation of the first shape;

altering, by the at least one computing device in response to at least one selection received in the graphical user interface, the orientation of the second shape to match the orientation of the first shape; and altering, as a function of the altered orientation of the second shape, the orientation of the endoscopic image provided on a display device.

2. The method of claim 1, wherein the first and second markers are asymmetric markers and the first and second shapes pie-shape wedges.

3. The method of claim 1, wherein altering the orientation of the endoscopic image includes rotating the endoscopic image to place at least the superior aspect at a 12 o'clock position.

4. The method of claim 1, wherein the image of the catheter is received from a fluoroscopy device.

5. The method of claim 1, wherein the at least one control comprises one or more of a graphical knob, graphical button, and graphical menu option.

6. A computer implemented system for altering an orientation of an endoscopic image received during a surgical procedure, the system comprising:

at least one computing device that is configured with one or more instructions that, when executed, cause the at least one computing device to:

provide, via a graphical user interface, an image of a catheter configured with a first marker and captured during a surgical procedure, wherein the catheter is in a respective orientation;

provide, via the graphical user interface, a second marker that corresponds to the first marker and is rotatable as a function of at least one control included in the graphical user interface, wherein the second marker appears in an orientation that is different than an orientation of the catheter;

alter, in response to at least one selection received in the graphical user interface, the orientation of the second marker to match the orientation of the catheter;

automatically provide, via the graphical user interface in response to the altered orientation of the second marker, a first shape that represents at least an obstructed portion of the endoscopic image, wherein the first shape is in a respective orientation;

provide, via the graphical user interface, a representation of a second shape that is rotatable as a function of at least one control included in the graphical user interface, wherein the second shape appears in an orientation that is different than the orientation of the first shape;

alter, in response to at least one selection received in the graphical user interface, the orientation of the second shape to match the orientation of the first shape; and alter, as a function of the altered orientation of the second shape, the orientation of the endoscopic image provided on a display device.

7. The system of claim 6, wherein the first and second markers are asymmetric markers and the first and second shapes are pie-shape wedges.

8. The system of claim 6, wherein altering the orientation of the endoscopic image includes rotating the endoscopic image to place at least the superior aspect at a 12 o'clock position.

9. The system of claim 6, wherein the image of the catheter is received from a fluoroscopy device.

10. The system of claim 6, wherein the at least one control comprises one or more of a graphical knob, graphical button, and graphical menu option.

* * * * *